United States Patent [19]

Levitt

[11] Patent Number: 4,655,822

[45] Date of Patent: * Apr. 7, 1987

[54] HERBICIDAL SULFONAMIDES

[75] Inventor: George Levitt, Wilmington, Del.

[73] Assignee: E. I. Du Pont de Nemours and Company, Wilmington, Del.

[ * ] Notice: The portion of the term of this patent subsequent to Jul. 13, 1999 has been disclaimed.

[21] Appl. No.: 671,875

[22] Filed: Nov. 15, 1984

Related U.S. Application Data

[63] Continuation of Ser. No. 424,477, Sep. 27, 1982, abandoned, which is a continuation-in-part of Ser. No. 187,174, Sep. 15, 1980, abandoned, which is a continuation of Ser. No. 840,167, Oct. 6, 1977, Pat. No. 4,257,802.

[51] Int. Cl.$^4$ ................... A01N 47/36; C07D 239/42
[52] U.S. Cl. ........................................ 71/92; 544/321; 544/332

[58] Field of Search ..................... 544/321, 332; 71/92

[56] References Cited

U.S. PATENT DOCUMENTS

| | | | |
|---|---|---|---|
| 4,169,719 | 10/1979 | Levitt | 71/92 |
| 4,214,890 | 7/1980 | Levitt | 71/90 |
| 4,310,346 | 1/1982 | Levitt et al. | 71/92 |
| 4,339,266 | 7/1982 | Levitt et al. | 71/92 |
| 4,370,480 | 1/1983 | Levitt et al. | 544/320 |
| 4,371,391 | 2/1983 | Levitt et al. | 71/93 |

FOREIGN PATENT DOCUMENTS 9419 4/1980 European Pat. Off. ............... 71/92

Primary Examiner—Robert Gerstl

[57] ABSTRACT

N-(heterocyclicaminocarbonyl)arylsulfonamides in which at least one of the acyclic nitrogens thereof is substituted by lower alkyl, are useful for the regulation of plant growth and as general and selective herbicides.

29 Claims, No Drawings

HERBICIDAL SULFONAMIDES

CROSS-REFERENCE TO RELATED APPLICATIONS

This is a continuation of application Ser. No. 424,477, filed Sept. 27, 1982, now abandoned, which is a continuation-in-part of application Ser. No. 187,174, filed Sept. 15, 1980, now abandoned, which is a continuation of application Ser. No. 840,167, filed Oct. 6, 1977, now U.S. Pat. No. 4,257,802.

BACKGROUND OF THE INVENTION

This invention relates to novel N-(heterocyclicaminocarbonyl)arylsulfonamides in which at least one of the acyclic nitrogens thereof is substituted by a moiety which may be lower alkyl, or in some cases by methoxy. The compounds of this invention and their agriculturally suitable salts, are useful as agricultural chemicals, such as plant growth regulants and herbicides.

Netherlands Patent No. 121,788, published Sept. 15, 1966, discloses the preparation of compounds of the following Formula and their use as general or selective herbicides,

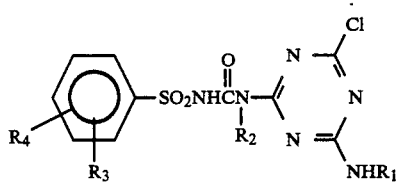

wherein
$R_1$ and $R_2$ may independently be alkyl of 1–4 carbon atoms; and
$R_3$ and $R_4$ may independently be hydrogen, chlorine or alkyl of 1–4 carbon atoms.

U.S. Pat. No. 3,637,366 discloses compounds having the formula:

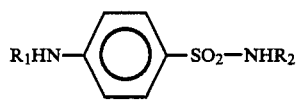

wherein
$R_1$ is hydrogen or lower saturated aliphatic acyl; and
$R_2$ is hydrogen, 2-pyrimidinyl, pyridyl, amidino, acetyl or carbamoyl.

The disclosed compounds are said to provide control of crabgrass, cress, endive, clover and *Poa annua*.

French Patent No. 1,468,747 discloses the following para-substituted phenylsulfonamides as being useful as antidiabetic agents:

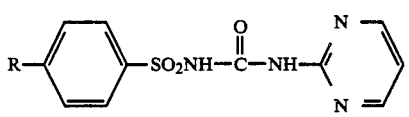

wherein R=H, halogen, $CF_3$ or alkyl.

Compounds of the following formula, and their use as antidiabetic agents, are reported in *J. Drug Res.* 6, 123 (1974)

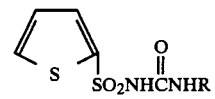

wherein R is pyridyl.

Logemann et al. Chem Ab., 53, 18052 g (1959), disclose a number of sulfonamides, including uracil derivatives and those having the formula:

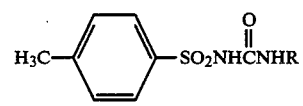

wherein R is butyl, phenyl or

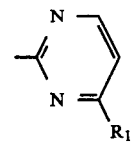

and $R_1$ is hydrogen or methyl. When tested for hypoglycemic effect in rats (oral doses of 25 mg/100 g), the compounds in which R is butyl and phenyl were most potent. The others were of low potency or inactive.

Wojciechowski, J. Acta. Polon. Pharm 19, p. 121-5 (1962) [Chem. Ab., 59 1633 e] describes the synthesis of N-[(2,6-dimethoxypyrimidin-4-yl)aminocarbonyl]-4-methylbenzenesulfonamide:

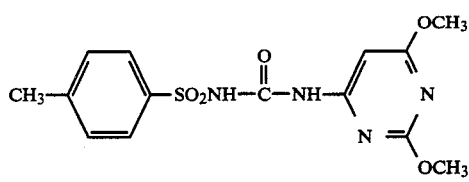

Based upon similarity to a known compound, the author predicted hypoglycemic activity for the foregoing compound.

Substituted-pyrimidinyl sulfonylureas of the following formula, which are also para-substituted on the phenyl ring, are disclosed in Farmco Ed. Sci., 12, 586 (1957) [Chem. Ab., 53, 18052 g (1959)]:

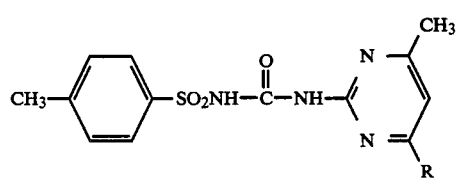

wherein R=H or $CH_3$.

In EPO application No. 78 3004682, published Apr. 18, 1977, there is taught agricultural compounds of the following formula:

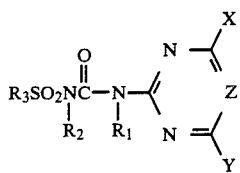

(I)

wherein
$R_1$ is H, alkyl of one to three carbon atoms or —$OCH_3$;
$R_2$ is H or alkyl of one to three carbon atoms;
$R_3$ is

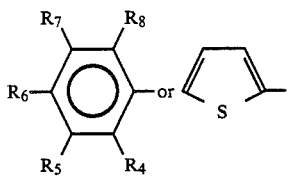

$R_4$ and $R_7$ are independently hydrogen, fluorine, chlorine, bromine, alkyl of 1–4 carbon atoms, alkoxy of 1–4 carbon atoms, nitro, $CF_3$ $CH_3S$— or $CH_3CH_2S$;

$R_5$, $R_6$ and $R_8$ are independently hydrogen, fluorine, chlorine, bromine or methyl;

X is Cl, $CH_3$, —$CH_2CH_3$, alkoxy of one to three carbons, $CF_3$, $CH_3S$—, $CH_3OCH_2$— or $CH_3OCH_2CH_2O$—;

Y is $CH_3$ or $OCH_3$;

Z is CH or N;

and their agriculturally suitable salts; provided that:
(a) $R_1$ and $R_2$ may not simultaneously be hydrogen; and
(b) when $R_4$ and $R_8$ are both hydrogen, at least one of $R_5$, $R_6$ or $R_7$ must be hydrogen;
(c) when $R_6$ is other than H, at least one or $R_4$, $R_5$, $R_7$ and $R_8$ is other than H and at least two of $R_4$, $R_5$, $R_7$ and $R_8$ must be hydrogen; and
(d) when $R_6$ is H and all of $R_4$, $R_5$, $R_7$ and $R_8$ are other than H, then all of $R_4$, $R_5$, $R_7$ and $R_8$ must be either Cl or $CH_3$.

The presence of undesired vegetation causes substantial damage to useful crops, especially agricultural products that satisfy man's basic food and fiber needs, such as cotton, rice, corn, wheat, and the like. The current population explosion and concomitant world food and fiber shortage demand improvements in the efficiency of producing these crops. Preventing or minimizing loss of a portion of such valuable crops by killing, or inhibiting the growth or undesired vegetation is one way of improving this efficiency.

A wide variety of materials useful for killing or inhibiting (controlling) the growth of undesired vegetation is available; such materials are commonly referred to as herbicides. However, the need still exists for effective herbicides that destroy or control weeds while not significantly damaging useful crops. Some weeds (nutsedge is a particular example) are very difficult to control; many of the herbicides that are used to control nutsedge are so nonselective that they cause damage to the crops themselves.

SUMMARY OF THE INVENTION

This invention related to compounds of Formula I and their agriculturally useful salts, compositions containing them and methods of using them as general and selective pre-emergence herbicides and as plant growth regulants.

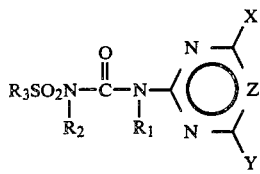

(I)

wherein
$R_1$ is H, alkyl of one to three carbon atoms or —$OCH_3$;
$R_2$ is H or alkyl of one to three carbon atoms;
$R_3$ is

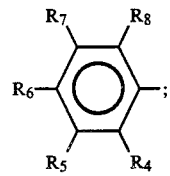

$R_7$ is hydrogen, fluorine, chlorine, bromine, alkyl of 1–4 carbon atoms, alkoxy of 1–4 carbon atoms, nitro, $CF_3$, $CH_3S$ or $CH_3CH_2S$;

$R_4$ is $R_9S(O)_n$;

$R_5$, $R_6$ and $R_8$ are independently hydrogen, fluorine, chlorine, bromine, methyl or methoxy;

$R_9$ is $C_1$–$C_4$ alkyl, $C_3$–$C_4$ alkenyl, cyclopentyl or cyclopropylmethyl;

X is $CH_3$, —$CH_2CH_3$, alkoxy of one to three carbons, $CF_3$, $CH_3S$—, $CH_3OCH_2$— or $CH_3OCH_2CH_2O$—;

Y is $CH_3$ or $OCH_3$;

Z is CH or N; and n is 0, 1 or 2;

and their agriculturally suitable salts; provided that:
(a) $R_1$ and $R_2$ mat not simultaneously be hydrogen;
(b) when $R_6$ is other than H, then $R_5$, $R_7$ and $R_8$ must be hydrogen;
(c) when n is 1, then $R_7$ is other than $CH_3S$ or $CH_3CH_2S$, and X is other than $CH_3S$;
(d) when $R_6$ is H and $R_5$, $R_7$ and $R_8$ are other than H, then $R_5$, $R_7$ and $R_8$ must either be Cl or $CH_3$; and
(e) when $R_9$ is $C_1$–$C_2$ alkyl, then n is 1 or 2.

Preferred in increasing order for their higher activity and/or more favorable ease of synthesis are:

(1) Compounds of the generic scope wherein $R_7$ is H, Cl, F, Br, $CH_3$, $OCH_3$, $CF_3$ or $NO_2$, and $R_1$ is H or $CH_3$;

(2) Compounds of Preferred (1) wherein $R_5$, $R_6$ and $R_8$ are H;

(3) Compounds of Preferred (2) wherein $R_2$ is H or $CH_3$;

(4) Compounds of Preferred (3) wherein X is $CH_3$, $OCH_3$, $OC_2H_5$ or $CH_2OCH_3$;

(5) Compounds of Preferred (4) wherein $R_9$ is $C_1$–$C_4$ alkyl and n is 2;

(6) Compounds of Preferred (5) wherein $R_7$ is H;

(7) Compounds of Preferred (6) wherein $R_2$ is H and $R_1$ is $CH_3$; and (8) Compounds of Preferred (7) wherein $R_9$ is $CH_3$.

Specifically preferred for highest activity and/or most favorable ease of synthesis are:

N-[(4,6-dimethoxypyrimidin-2-yl)(methyl)aminocarbonyl]-2-(methylsulfonyl)benzenesulfonamide;
N-[(4,6-dimethylpyrimidin-2-yl)(methyl)aminocarbonyl]-2-(methylsulfonyl)benzenesulfonamide;
N-[(4-methyl-6-methoxypyrimidin-2-yl)(methyl)aminocarbonyl]-2-(methylsulfonyl)benzenesulfonamide;
N-[(4,6-dimethoxy-1,3,5-triazin-2-yl)(methyl)aminocarbonyl]-2-(methylsulfonyl)benzenesulfonamide;
N-[(4,6-dimethyl-1,3,5-triazin-2-yl)(methyl)aminocarbonyl]-2-(methylsulfonyl)benzenesulfonamide;
N-[(4-methyl-6-methoxy-1,3,5-triazin-2-yl)(methyl)aminocarbonyl]-2-(methylsulfonyl)benzenesulfonamide;
N-[(4,6-dimethoxypyrimidin-2-yl)(methyl)aminocarbonyl]-2-(propylsulfonyl)benzenesulfonamide;
N-[(4,6-dimethoxy-1,3,5-triazin-2-yl)(methyl)aminocarbonyl]-2-(propylsulfonyl)benzenesulfonamide; and
N-[(4-methoxy-6-methyl-1,3,5-triazin-2-yl)(methyl)aminocarbonyl]-2-(propylsulfonyl)benzenesulfonamide.

This invention also relates to compounds of Formula II which are useful as intermediates for the compounds of Formula I.

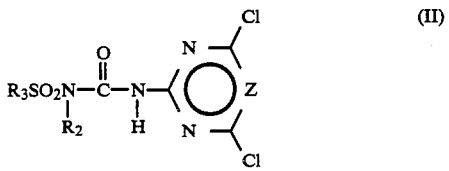

(II)

wherein
$R_2$ is alkyl of one to three carbon atoms;
$R_3$ is

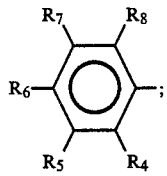

$R_7$ is hydrogen, fluorine, chlorine, bromine, alkyl of 1-4 carbon atoms, alkoxy of 1-4 carbon atoms, nitro, $CF_3$, $CH_3S$ or $CH_3CH_2S$;
$R_4$ is $R_9S(O)_n$;
$R_5$, $R_6$ and $R_8$ are independently hydrogen, fluorine, chlorine, bromine, methyl or methoxy;
$R_9$ is $C_1-C_4$ alkyl, $C_3-C_4$ alkenyl, cyclopentyl or cyclopropylmethyl;
Z is CH or N;
n is 0 or 2;
provided that
(a) when $R_6$ is other than H, then $R_5$, $R_7$ and $R_8$ must be hydrogen; and
(b) when $R_6$ is H and $R_5$, $R_7$ and $R_8$ are other than H, then $R_5$, $R_7$ and $R_8$ must either be Cl or $CH_3$.

Synthesis

As shown in Equation 1, the compounds of Formula I, wherein $R_2$ is H and $R_4 \neq R_9SO$ can be prepared by reacting an appropriately substituted sulfonyl isocyanate of Formula III with an appropriate 2-alkylaminopyrimidine or 2-alkylamino-1,3,5-triazine of Formula IV, $R_1$, $R_3$, X, Y and Z being as previously defined.

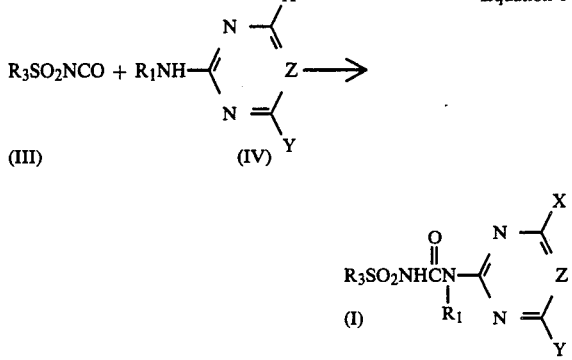

Equation 1

The reaction is best carried out in inert aprotic organic solvents such as methylene chloride, tetrahydrofuran or acetonitrile, at ambient pressure and temperature. The mode of addition is not critical; however, it is often convenient to add the sulfonyl isocyanate to a stirred suspension of amine III. Since such isocyanates are usually liquids, their addition can be easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane or ethyl ether, and filtration.

The intermediate sulfonyl isocyanates of Formula III wherein $n \neq 1$ can be prepared as shown in Equation 2 by reacting the corresponding sulfonamides of Formula V with phosgene in the presence of n-butyl isocyanate at reflux in a solvent such as xylene, according to the procedure of H. Ulrich and A. A. Y. Sayigh, *Newer Methods of Preparative Organic Chemistry*, Vol. VI, p. 223–241, Academic Press, New York and London, W. Foerst Ed. In cases where formation of the desired sulfonyl isocyanate is difficult by the above procedure, the sulfonylurea formed by the reaction of butyl isocyanate with the appropriate sulfonamide is treated with phosgene according to the above reference.

Equation 2

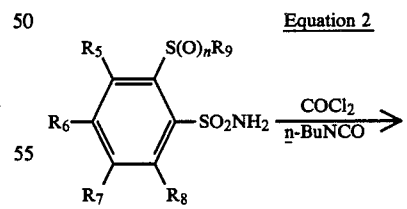

(V)

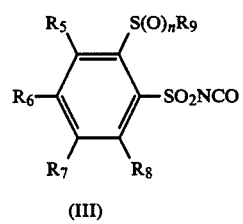

(III)

The sulfonamides of Formula V wherein n≠1 can be prepared by a variety of procedures reported in the literature. As shown in Equation 3, the thioether of Formula VI may be prepared from the appropriate 2-aminothiophenol and an alkyl halide as described in the literature, e.g. R. N. Prasad, et al. *Can. J. Chem.* 44, 1247 (1966). The formation of the benzenesulfonyl chloride and the corresponding sulfonamide Va has been previously described (co-pending application U.S. 192,034, filed Sept. 29, 1980). The oxidation of Va to the corresponding 2-alkylsulfonylbenzenesulfonamides of Formula Vb may be carried out utilizing a variety of standard literature procedures with m-chloroperbenzoic acid (C. R. Johnson, et al., *Tetrahedron* 25, 5649 (1969)), or with aqueous hydrogen peroxide in acetic acid (F. G. Bordwell, et al., *J. Amer. Chem. Soc.* 77, 1141 (1955)).

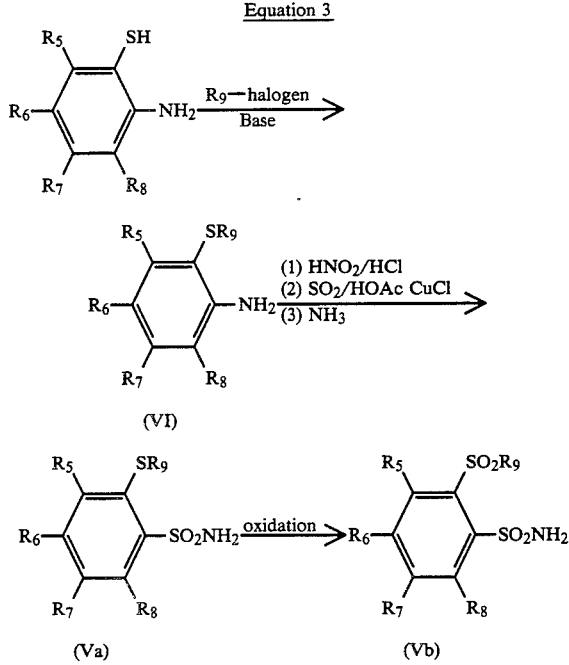

Equation 3

(VI)

(Va)  (Vb)

Compounds of Formula V wherein n≠1 may also be prepared from 2-halonitrobenzenes of Formula VII as outlined in Equation 4. Halide displacement in VII by thiols (n=0) or sulfinates (n=2) is widely reported in the literature (for general reviews see, "Organic Chemistry of Sulfur", S. Oae, ed., Plenum Press, New York, 1977, pp. 232-233; Reid, "Organic Chemistry of Bivalent Sulfur," Chemical Publishing Co., New York, Vol. 2, pp. 16-21, 24-29; Vol. 3, pp. 11-14; Peach, in Patai, "The Chemistry of the Thiol Group," pt. 2, pp. 735-744, John Wiley and Sons, Inc., New York, 1974).

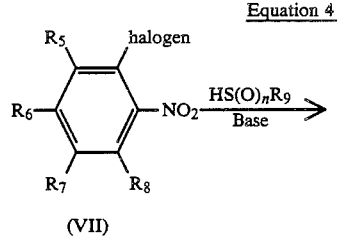

Equation 4

(VII)

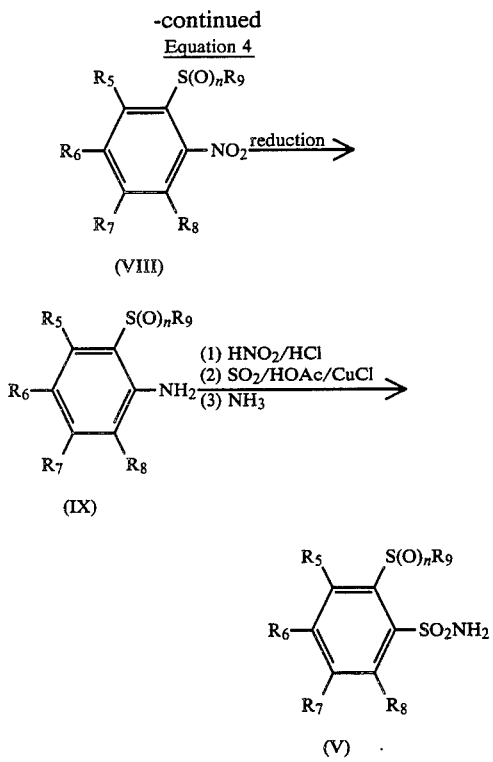

Equation 4 -continued (VIII)

(IX)

(V)

Compounds of Formula VIII may also be prepared as shown in Equation 5 [in addition to references cited above, see, *Zh. Obshch. Khim.*, 35 (8) 1361 (1965) and *J. Chem. Soc.*, 763 (1946)]. Reduction of VIII to the amine IX can be carried out by a variety of standard literature procedures, including catalytic hydrogenation (Rylander, "Catalytic Hydrogenation over Platinum Metals," pp. 168-202, Academic Press, Inc., New York, 1967) and reduction with iron (D. Cowsley et al., *Synthesis* 118 (1977)) or stannous chloride [*Org. Synth.*, Coll. Vol. 2, 130 (1943); ibid, 3, 240, 453 (1955)] in acidic medium.

Equation 5

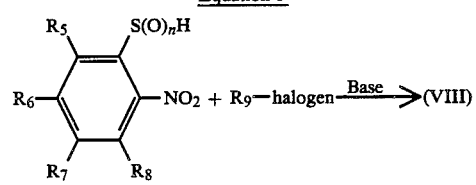

Ortho-lithiation of appropriately substituted benzene derivatives also provides a route to sulfonamides of Formula V. As shown in Equation 6, the t-butylbenzenesulfonamides of Formula X may be ortho-lithiated [for general review, see H. W. Gschwend et. al., *Organic Reactions*, 26, 1 (1979)] and then trapped with sulfur, followed by alkyl halide, or disulfide to give sulfonamides of Formula Va [S. Gronowitz et al., *Acta, Chem. Scand.* 21, 812 (1967) and *Chem. Ber.* 99, 3215 (1966)]. Treatment of XI with sulfur dioxide, followed by alkyl halide will give sulfonamides of Formula Vb [*JACS*, 74, 5177 (1952)].

Equation 6

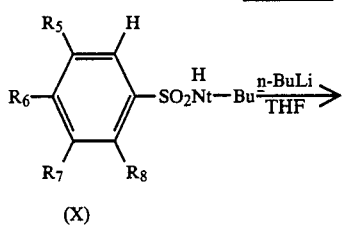

(X)

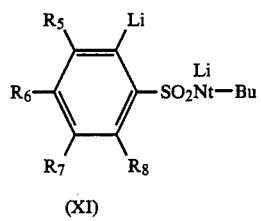

(XI)

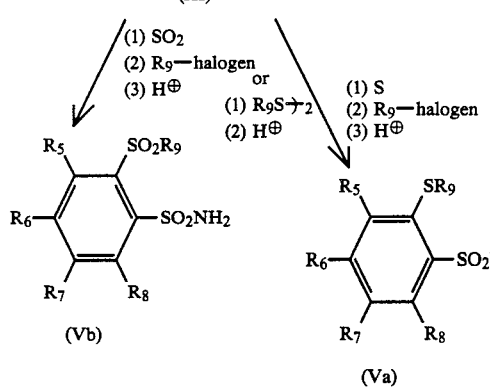

(Vb)                (Va)

The lithium sulfonates of Formula XII can also be ortho-lithiated to give compounds of Formula XIII as shown in Equation 7. Treatment of XIII with sulfur electrophiles as in Equation 6 will give the sulfonates of Formula XIV [for example, see J. C. Martin et al., *JOC*, 45, 3728 (1980)]. Conversion of XIV to the sulfonamides of Formula V can be accomplished using thionyl chloride and a catalytic amount of dimethylformamide and then treating the sulfonyl chloride with ammonia.

Equation 7

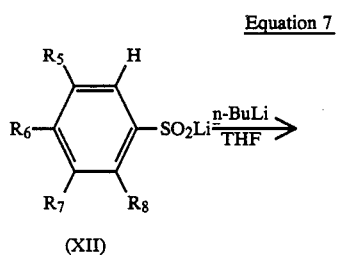

(XII)

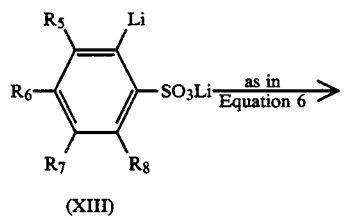

(XIII)

-continued
Equation 7

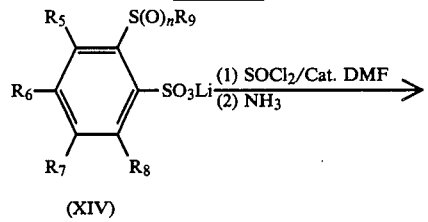

(XIV)

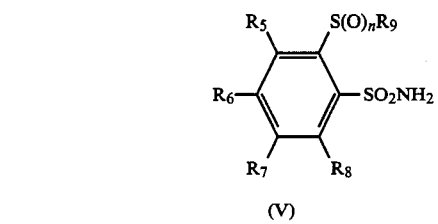

(V)

Compounds of Formula I, wherein $R_2$ is alkyl, can be prepared by alkylation of the salts of compounds of Formula I, wherein $R_2$ is H, as shown in Equation 8 $R_1$, $R_2$, $R_3$, X, Y and Z being as previously defined and M is a metal cation and Q an anion, such as halide or sulfate.

Equation 8

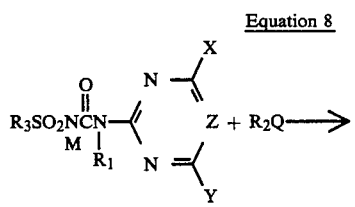

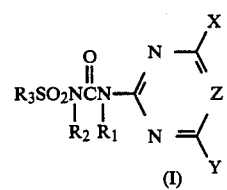

(I)

The reaction is best carried out in aprotic organic solvents such as tetrahydrofuran, dimethylformamide, or dimethylacetamide, at ambient pressure and temperature. Alkylating agents such as dimethyl sulfate, methyl iodide, and ethyl iodide can be employed. The desired product can be isolated by pouring the reaction mixture into water and filtering off the precipitated solid.

Alternatively, compounds of Formula I, wherein $R_2$ is alkyl and $R_4 \neq R_9SO$, can be prepared by the reaction of an appropriately substituted sulfonyl-N-alkylcarbamyl chloride of Formula XV with an appropriate 2-aminopyrimidine or 2-amino-1,3,5-triazine of Formula IV as shown in Equation 9 $R_1$, $R_2$, $R_3$, X, Y and Z are as previously defined.

Equation 9

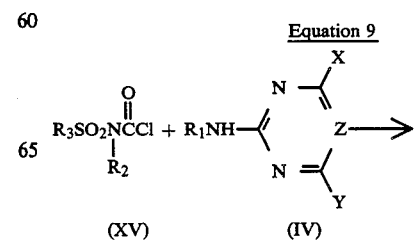

(XV)            (IV)

-continued
Equation 9

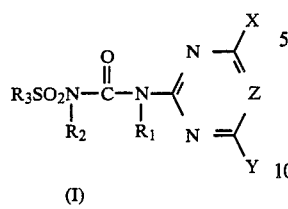

(I)

The preparation of ureas from amines and carbamyl chlorides is well known to the art. The reaction can best be carried out by adding equivalent amounts of a carbamyl chloride, XV, and amine, IV, to an inert organic solvent, such as tetrahydrofuran, xylene, or methylene chloride, in the presence of an acid acceptor, such as triethylamine, pyridine, or sodium carbonate, employing temperatures from 20° to 130°. Soluble products can be isolated by filtering off precipitated salts and concentration of the filtrate. Insoluble products can be filtered off and washed free of salts with water.

The intermediate sulfonyl-N-alkyl carbamyl chlorides of Formula XV can be prepared by phosgenation of N-alkylsulfonamide salts. The sulfonamide salt is added to an excess of phosgene in an inert organic solvent, such as tetrahydrofuran, toluene, or xylene, whereupon the carbamyl chloride can be isolated or reacted in situ with the amine, IV, after removal of the excess phosgene.

Compounds of Formula Ib wherein $R_4=R_9SO$ can be prepared from the appropriate compounds of Formula Ia wherein $R_4=R_9S$ by oxidation with m-chloroperbenzoic acid as shown in Equation 10. The reaction can be carried out by stirring equivalent amounts of Ia with m-chloroperbenzoic acid (MCPBA) in an inert solvent such as chloroform at 0° to reflux for 12-24 hours. The insoluble m-chlorobenzoic acid produced is removed by filtration and the chloroform solution is concentrated to yield the crude product. Purification by standard techniques will give the desired product. Oxidation of Ia with one equivalent of hydrogen peroxide in acetic acid at room temperature will also give the sulfoxides Ib.

Equation 10

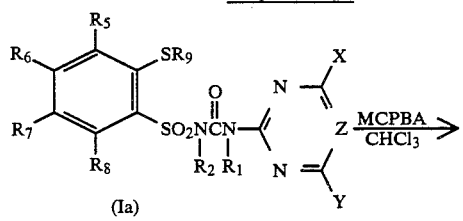

(Ia)

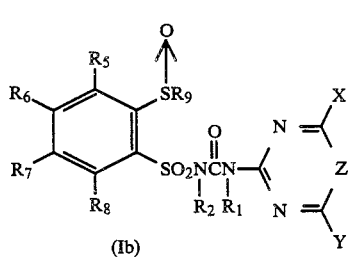

(Ib)

Compounds of Formula Ic can also be prepared from intermediates of Formula II by reaction with sodium methoxide in methanol as shown in Equation 11.

Equation 11

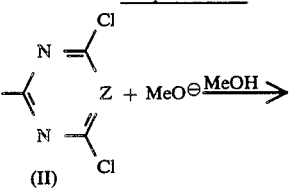

(II)

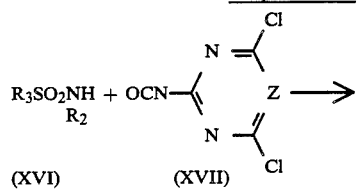

(Ic)

The intermediates of Formula II can be synthesized from the sulfonamides XVI and the heterocyclic isocyanates of Formula XVII as outlined in Equation 12. The preparation of heterocyclic isocyanates of Formula XVII is well documented in the literature [U.S. Pat. No. 3,849,413 and Angew. Chem. Int. Ed. Eng., 10, 402 (1976)].

Equation 12

$$R_3SO_2NH + OCN\text{—heterocycle}$$
$R_2$
(XVI)    (XVII)

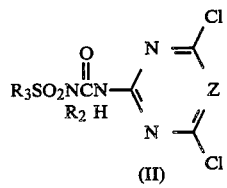

(II)

The synthesis of heterocyclic amine derivatives has been reviewed in "The Chemistry of Heterocyclic Compounds," a series published by Interscience Publ., New York and London. 2-Aminopyrimidines are described by D. J. Brown in "The Pyrimidines", Vo . . . XVI of the above series. 2-Amino-1,3,5-triazines can be synthesized according to the methods described by E. M. Smolin and L. Rapaport in "s-Triazines and Derivatives," Vol. XIII of the same series. N-Methoxyaminoheterocycles can be prepared by procedures reported in the literature [for example, see Belg. 618,563 and J. T. Shaw et al., JOC, 27, 4054 (1962)].

The preparation of agriculturally suitable salts of the compounds of Formula I, as well as starting materials and intermedaites for said compounds is disclosed in my U.S. Pat. No. 4,169,719, the contents of which are incorporated by reference.

The compounds of this invention and their preparation are further illustrated by the following examples wherein temperatures are given in degrees centigrade and all parts are by weight unless otherwise indicated.

EXAMPLE 1

N-[(4,6-Dimethoxy-1,3,5-triazin-2-yl)(methoxy)aminocarbonyl]-2-(methylsulfonyl)benzenesulfonamide To a stirred suspension of N,4,6-trimethoxy-1,3,5-triazin-2-amine (0.01 mol) in dry methylene chloride (24 ml) is added 2-methylsulfonylbenzenesulfonyl isocyanate (0.014 mol). The mixture is stirred at ambient temperature for 24 hours. The solvent is then evaporated under reduced pressure. The residue is stirred in 1-chlorobutane (50 ml) for 5 hours. The solid is then filtered, washed with ether and dried to yield N-[(4,6-dimethoxy-1,3,5-triazin-2-yl)(methoxy)aminocarbonyl]-2-(methylsulfonyl)benzenesulfonamide.

EXAMPLE 2

N-[(4,6-dimethoxy-1,3,5-triazin-2-yl)(methyl)aminocarbonyl]-2-(methylsulfonyl)benzenesulfonamide A solution of 2-methylsulfonylbenzenesulfonylisocyanate (2.1 g, 8.0 mmol) in dry methylene chloride (12 ml) was added to 2-methylamino-4,6-dimethoxy-1,3,5-triazine (1.0 g, 6.0 mmol) and a catalytic amount of 1,4-diaza[2.2.2]bicyclooctane. The mixture was stirred at room temperature overnight. The solvent was removed in-vacuo and 1-chlorobutane was added to the residue. The precipitated solid was filtered and dried to give N-[(4,6-dimethoxy-1,3,5-triazin-2-yl)(methyl)aminocarbonyl]-2-(methylsulfonyl)benzenesulfonamide (2.3 g) as a white powder, m.p. 160°-162.5°. The product showed characteristic singlets in the NMR at $\delta$3.25 (NCH$_3$), 3.40 (SO$_2$CH$_3$) and 4.0 (OCH$_3$), and showed infrared absorption peaks at 1690, 1550, 1420, 1340, 1310 and 1150 cm$^{-1}$.

By using procedures apparent from those given in Examples 1 and 2, the compounds of Formula I set forth in Tables I and II can be prepared.

TABLE I-A

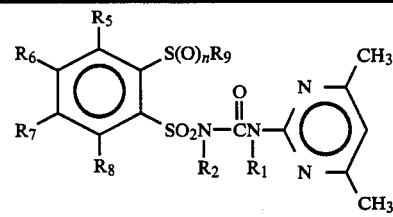

| R$_1$ | R$_2$ | R$_5$ | R$_6$ | R$_7$ | R$_8$ | R$_9$ | n |
|---|---|---|---|---|---|---|---|
| CH$_3$ | H | H | H | H | H | CH$_3$ | 1 |
| CH$_3$ | H | H | H | H | H | CH$_3$ | 2 |
| CH$_3$ | H | H | H | H | H | CH$_2$CH$_3$ | 1 |
| CH$_3$ | H | H | H | H | H | CH$_2$CH$_3$ | 2 |
| CH$_3$ | H | H | H | H | H | CH$_2$CH$_2$CH$_3$ | 0 |
| CH$_3$ | H | H | H | H | H | CH$_2$CH$_2$CH$_3$ | 1 |
| CH$_3$ | H | H | H | H | H | CH$_2$CH$_2$CH$_3$ | 2 |
| CH$_3$ | H | H | H | H | H | CH(CH$_3$)$_2$ | 0 |
| CH$_3$ | H | H | H | H | H | CH(CH$_3$)$_2$ | 1 |
| CH$_3$ | H | H | H | H | H | CH(CH$_3$)$_2$ | 2 |
| CH$_3$ | H | H | H | H | H | CH$_2$CH=CH$_2$ | 0 |
| CH$_3$ | H | H | H | H | H | CH$_2$CH=CH$_2$ | 1 |
| CH$_3$ | H | H | H | H | H | CH$_2$CH=CH$_2$ | 2 |
| CH$_3$ | H | H | H | H | H | CH=CHCH$_3$ | 0 |
| CH$_3$ | H | H | H | H | H | CH=CHCH$_3$ | 1 |
| CH$_3$ | H | H | H | H | H | CH=CHCH$_3$ | 2 |
| CH$_3$ | H | H | H | H | H | CH=CHCH$_2$CH$_3$ | 0 |
| CH$_3$ | H | H | H | H | H | CH=CHCH$_2$CH$_3$ | 1 |
| CH$_3$ | H | H | H | H | H | CH=CHCH$_2$CH$_3$ | 2 |
| CH$_3$ | H | H | H | H | H | CH$_2$CH=CH$_2$CH$_3$ | 0 |
| CH$_3$ | H | H | H | H | H | CH$_2$CH=CH$_2$CH$_3$ | 1 |
| CH$_3$ | H | H | H | H | H | CH$_2$CH=CH$_2$CH$_3$ | 2 |
| CH$_3$ | H | H | H | H | H | -cyclopentyl | 0 |
| CH$_3$ | H | H | H | H | H | -cyclopentyl | 1 |
| CH$_3$ | H | H | H | H | H | -cyclopentyl | 2 |
| CH$_3$ | H | H | H | H | H | -CH$_2$-cyclopropyl | 0 |

TABLE I-A-continued

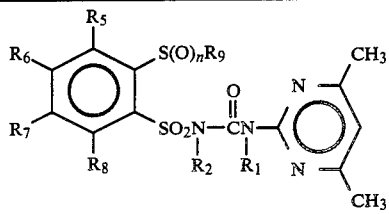

| R1 | R2 | R5 | R6 | R7 | R8 | R9 | n |
|---|---|---|---|---|---|---|---|
| $CH_3$ | H | H | H | H | H | $CH_2$-cyclopropyl | 1 |
| $CH_3$ | H | H | H | H | H | $CH_2$-cyclopropyl | 2 |
| $CH_2CH_3$ | H | H | H | H | H | $CH_3$ | 2 |
| $CH_2CH_2CH_3$ | H | H | H | H | H | $CH_3$ | 2 |
| $CH(CH_3)_2$ | H | H | H | H | H | $CH_3$ | 2 |
| $CH_2CH_3$ | $CH_3$ | H | H | H | H | $CH_3$ | 2 |
| $CH_2CH_2CH_3$ | $CH_3$ | H | H | H | H | $CH_3$ | 2 |
| $CH(CH_3)_2$ | $CH_3$ | H | H | H | H | $CH_3$ | 2 |
| $CH_3$ | $CH_2CH_3$ | H | H | H | H | $CH_3$ | 2 |
| $CH_3$ | $CH_2CH_2CH_3$ | H | H | H | H | $CH_3$ | 2 |
| $CH_3$ | $CH(CH_3)_2$ | H | H | H | H | $CH_3$ | 2 |
| $OCH_3$ | $CH_2CH_3$ | H | H | H | H | $CH_3$ | 2 |
| $OCH_3$ | $CH_2CH_2CH_3$ | H | H | H | H | $CH_3$ | 2 |
| $OCH_3$ | $CH(CH_3)_2$ | H | H | H | H | $CH_3$ | 2 |
| $OCH_3$ | $CH_3$ | H | H | H | H | $CH_3$ | 2 |
| $CH_3$ | H | H | H | F | H | $CH_3$ | 2 |
| $CH_3$ | H | H | H | Cl | H | $CH_3$ | 2 |
| $CH_3$ | H | H | H | $CH_3$ | H | $CH_3$ | 2 |
| $CH_3$ | H | H | H | $OCH_3$ | H | $CH_3$ | 2 |
| $CH_3$ | H | H | H | $CH_2CH_3$ | H | $CH_3$ | 2 |
| $CH_3$ | H | H | H | $CH(CH_3)_2$ | H | $CH_3$ | 2 |
| $CH_3$ | H | H | H | $CH_2CH_2CH_3$ | H | $CH_3$ | 2 |
| $CH_3$ | H | H | H | $CH_2CH_2CH_2CH_3$ | H | $CH_3$ | 2 |
| $CH_3$ | H | H | H | $CH_2CH(CH_3)_2$ | H | $CH_3$ | 2 |
| $CH_3$ | H | $CH_3$ | H | H | H | $CH_3$ | 2 |
| $CH_3$ | H | $OCH_3$ | H | H | H | $CH_3$ | 2 |
| $CH_3$ | H | F | H | H | H | $CH_3$ | 2 |
| $CH_3$ | H | Cl | H | H | H | $CH_3$ | 2 |
| $CH_3$ | H | Br | H | H | H | $CH_3$ | 2 |
| $CH_3$ | H | H | H | H | $CH_3$ | $CH_3$ | 2 |
| $CH_3$ | H | H | H | H | $OCH_3$ | $CH_3$ | 2 |
| $CH_3$ | H | H | H | H | F | $CH_3$ | 2 |
| $CH_3$ | H | H | H | H | Cl | $CH_3$ | 2 |
| $CH_3$ | H | H | H | H | Br | $CH_3$ | 2 |
| H | $CH_3$ | H | H | H | H | $CH_3$ | 2 |
| H | $CH_3$ | H | H | H | H | $CH_2CH_3$ | 2 |
| H | $CH_3$ | H | H | H | H | $CH_2CH_2CH_3$ | 2 |
| H | $CH_3$ | H | H | H | H | $CH(CH_3)_2$ | 2 |
| H | $CH_3$ | H | H | H | H | $CH_2CH=CH_2$ | 2 |
| H | $CH_3$ | H | H | H | H | $CH=CHCH_3$ | 2 |
| H | $CH_3$ | H | H | H | H | $CH_2CH=CHCH_3$ | 2 |
| H | $CH_3$ | H | H | H | H | $CH=CHCH_2CH_3$ | 2 |
| H | $CH_3$ | H | H | H | H | $CH_2$-cyclopropyl | 2 |
| H | $CH_3$ | H | H | H | H | cyclopentyl | 2 |
| H | $CH_2CH_3$ | H | H | H | H | $CH_2CH_2CH_3$ | 2 |
| H | $CH_2CH_2CH_3$ | H | H | H | H | $CH_2CH_2CH_3$ | 2 |
| H | $CH(CH_3)_2$ | H | H | H | H | $CH_2CH_2CH_3$ | 2 |
| $OCH_3$ | H | H | H | H | H | $CH_3$ | 2 |
| $OCH_3$ | H | H | H | H | H | $CH_2CH_3$ | 2 |
| $OCH_3$ | H | H | H | H | H | $CH_2CH_2CH_3$ | 2 |
| $OCH_3$ | H | H | H | H | H | $CH(CH_3)_2$ | 2 |
| $OCH_3$ | H | H | H | H | H | $CH_2CH=CH_2$ | 2 |
| $OCH_3$ | H | H | H | H | H | $CH=CHCH_3$ | 2 |
| $OCH_3$ | H | H | H | H | H | $CH_2CH=CHCH_3$ | 2 |

TABLE I-A-continued

[Structure diagram: substituted benzene ring with R5, R6, R7, R8 substituents, S(O)ₙR9 group, and SO2N(R2)-C(=O)-N(R1) linked to 4,6-dimethylpyrimidin-2-yl]

| $R_1$ | $R_2$ | $R_5$ | $R_6$ | $R_7$ | $R_8$ | $R_9$ | n |
|---|---|---|---|---|---|---|---|
| OCH₃ | H | H | H | H | H | CH=CHCH₂CH₃ | 2 |
| OCH₃ | H | H | H | H | H | CH₂—cyclopropyl | 2 |
| OCH₃ | H | H | H | H | H | cyclopentyl | 2 |
| CH₃ | CH₃ | H | H | H | H | CH₃ | 2 |
| CH₃ | CH₃ | H | H | H | H | CH₂CH₃ | 2 |
| CH₃ | CH₃ | H | H | H | H | CH₂CH₂CH₃ | 2 |
| CH₃ | CH₃ | H | H | H | H | CH(CH₃)₂ | 2 |
| CH₃ | CH₃ | H | H | H | H | CH=CHCH₃ | 2 |
| CH₃ | CH₃ | H | H | H | H | CH₂CH=CH₃ | 2 |
| CH₃ | CH₃ | H | H | H | H | CH=CHCH₂CH₃ | 2 |
| CH₃ | CH₃ | H | H | H | H | CH₂CH=CH₂CH₃ | 2 |
| CH₃ | CH₃ | H | H | H | H | CH₂—cyclopropyl | 2 |
| CH₃ | CH₃ | H | H | H | H | cyclopentyl | 2 |
| CH₃ | H | H | H | H | H | (CH₂)₃CH₃ | 0 |
| CH₃ | H | H | H | H | H | (CH₂)₃CH₃ | 1 |
| CH₃ | H | H | H | H | H | (CH₂)₃CH₃ | 2 |
| C₂H₅ | H | H | H | H | H | (CH₂)₃CH₃ | 0 |
| C₂H₅ | H | H | H | H | H | (CH₂)₃CH₃ | 1 |
| C₂H₅ | H | H | H | H | H | (CH₂)₃CH₃ | 2 |
| CH₃CH₂CH₂ | H | H | H | H | H | (CH₂)₃CH₃ | 0 |
| CH₃CH₂CH₂ | H | H | H | H | H | (CH₂)₃CH₃ | 1 |
| CH₃CH₂CH₂ | H | H | H | H | H | (CH₂)₃CH₃ | 2 |
| (CH₃)₂CH | H | H | H | H | H | (CH₂)₃CH₃ | 2 |
| H | CH₃ | H | H | H | H | (CH₂)₃CH₃ | 2 |
| CH₃ | H | H | CH₃ | H | H | (CH₃)₂CH₃ | 2 |
| CH₃ | H | H | CH₃ | H | CH₃ | (CH₂)₂CH₃ | 2 |
| CH₃ | H | F | H | H | H | (CH₂)₂CH₃ | 2 |
| CH₃ | H | Cl | H | H | H | (CH₂)₂CH₃ | 2 |
| CH₃ | H | Br | H | H | H | (CH₂)₂CH₃ | 2 |
| CH₃ | H | CH₃ | H | H | H | (CH₂)₂CH₃ | 2 |
| CH₃ | H | OCH₃ | H | H | H | (CH₂)₂CH₃ | 2 |
| CH₃ | H | H | F | H | H | (CH₂)₂CH₃ | 2 |
| CH₃ | H | H | Cl | H | H | (CH₂)₂CH₃ | 2 |
| CH₃ | H | H | Br | H | H | (CH₂)₂CH₃ | 2 |
| CH₃ | H | H | CH₃ | H | H | (CH₂)₂CH₃ | 2 |
| CH₃ | H | H | OCH₃ | H | H | (CH₂)₂CH₃ | 2 |
| CH₃ | H | H | H | H | Cl | (CH₂)₂CH₃ | 2 |
| CH₃ | H | H | H | H | F | (CH₂)₂CH₃ | 2 |
| CH₃ | H | H | H | H | Br | (CH₂)₂CH₃ | 2 |
| CH₃ | H | CH₃ | H | CH₃ | CH₃ | (CH₂)₂CH₃ | 2 |
| CH₃ | H | Cl | H | Cl | Cl | (CH₂)₂CH₃ | 2 |
| CH₃ | H | CH₃ | H | Cl | CH₃ | (CH₂)₂CH₃ | 2 |
| CH₃ | H | H | H | SCH₃ | H | (CH₂)₂CH₃ | 2 |
| CH₃ | H | H | H | SC₂H₅ | H | (CH₂)₂CH₃ | 2 |

TABLE I-B

[Structure: benzene ring with R5, R6, R7, R8 substituents, S(O)nR9 group, and SO2N(R2)-C(=O)-N(R1)-pyrimidine where pyrimidine has CH3 and OCH3 substituents]

| $R_1$ | $R_2$ | $R_5$ | $R_6$ | $R_7$ | $R_8$ | $R_9$ | n |
|---|---|---|---|---|---|---|---|
| CH$_3$ | H | H | H | H | H | CH$_3$ | 1 |
| CH$_3$ | H | H | H | H | H | CH$_3$ | 2 |
| CH$_3$ | H | H | H | H | H | CH$_2$CH$_3$ | 1 |
| CH$_3$ | H | H | H | H | H | CH$_2$CH$_3$ | 2 |
| CH$_3$ | H | H | H | H | H | CH$_2$CH$_2$CH$_3$ | 0 |
| CH$_3$ | H | H | H | H | H | CH$_2$CH$_2$CH$_3$ | 1 |
| CH$_3$ | H | H | H | H | H | CH$_2$CH$_2$CH$_3$ | 2 |
| CH$_3$ | H | H | H | H | H | CH(CH$_3$)$_2$ | 0 |
| CH$_3$ | H | H | H | H | H | CH(CH$_3$)$_2$ | 1 |
| CH$_3$ | H | H | H | H | H | CH(CH$_3$)$_2$ | 2 |
| CH$_3$ | H | H | H | H | H | CH$_2$CH=CH$_2$ | 0 |
| CH$_3$ | H | H | H | H | H | CH$_2$CH=CH$_2$ | 1 |
| CH$_3$ | H | H | H | H | H | CH$_2$CH=CH$_2$ | 2 |
| CH$_3$ | H | H | H | H | H | CH=CHCH$_3$ | 0 |
| CH$_3$ | H | H | H | H | H | CH=CHCH$_3$ | 1 |
| CH$_3$ | H | H | H | H | H | CH=CHCH$_3$ | 2 |
| CH$_3$ | H | H | H | H | H | CH=CHCH$_2$CH$_3$ | 0 |
| CH$_3$ | H | H | H | H | H | CH=CHCH$_2$CH$_3$ | 1 |
| CH$_3$ | H | H | H | H | H | CH=CHCH$_2$CH$_3$ | 2 |
| CH$_3$ | H | H | H | H | H | CH$_2$CH=CH$_2$CH$_3$ | 0 |
| CH$_3$ | H | H | H | H | H | CH$_2$CH=CH$_2$CH$_3$ | 1 |
| CH$_3$ | H | H | H | H | H | CH$_2$CH=CH$_2$CH$_3$ | 2 |
| CH$_3$ | H | H | H | H | H | cyclopentyl | 0 |
| CH$_3$ | H | H | H | H | H | cyclopentyl | 1 |
| CH$_3$ | H | H | H | H | H | cyclopentyl | 2 |
| CH$_3$ | H | H | H | H | H | CH$_2$-cyclopropyl | 0 |
| CH$_3$ | H | H | H | H | H | CH$_2$-cyclopropyl | 1 |
| CH$_3$ | H | H | H | H | H | CH$_2$-cyclopropyl | 2 |
| CH$_2$CH$_3$ | H | H | H | H | H | CH$_3$ | 2 |
| CH$_2$CH$_2$CH$_3$ | H | H | H | H | H | CH$_3$ | 2 |
| CH(CH$_3$)$_2$ | H | H | H | H | H | CH$_3$ | 2 |
| CH$_2$CH$_3$ | CH$_3$ | H | H | H | H | CH$_3$ | 2 |
| CH$_2$CH$_2$CH$_3$ | CH$_3$ | H | H | H | H | CH$_3$ | 2 |
| CH(CH$_3$)$_2$ | CH$_3$ | H | H | H | H | CH$_3$ | 2 |
| CH$_3$ | CH$_2$CH$_3$ | H | H | H | H | CH$_3$ | 2 |
| CH$_3$ | CH$_2$CH$_2$CH$_3$ | H | H | H | H | CH$_3$ | 2 |
| CH$_3$ | CH(CH$_3$)$_2$ | H | H | H | H | CH$_3$ | 2 |
| OCH$_3$ | CH$_2$CH$_3$ | H | H | H | H | CH$_3$ | 2 |
| OCH$_3$ | CH$_2$CH$_2$CH$_3$ | H | H | H | H | CH$_3$ | 2 |
| OCH$_3$ | CH(CH$_3$)$_2$ | H | H | H | H | CH$_3$ | 2 |
| OCH$_3$ | CH$_3$ | H | H | H | H | CH$_3$ | 2 |
| CH$_3$ | H | H | H | F | H | CH$_3$ | 2 |
| CH$_3$ | H | H | H | Cl | H | CH$_3$ | 2 |
| CH$_3$ | H | H | H | CH$_3$ | H | CH$_3$ | 2 |
| CH$_3$ | H | H | H | OCH$_3$ | H | CH$_3$ | 2 |

TABLE I-B-continued

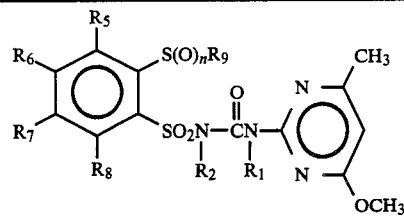

| R₁ | R₂ | R₅ | R₆ | R₇ | R₈ | R₉ | n |
|---|---|---|---|---|---|---|---|
| CH₃ | H | H | H | CH₂CH₃ | H | CH₃ | 2 |
| CH₃ | H | H | H | CH(CH₃)₂ | H | CH₃ | 2 |
| CH₃ | H | H | H | CH₂CH₂CH₃ | H | CH₃ | 2 |
| CH₃ | H | H | H | CH₂CH₂CH₂CH₃ | H | CH₃ | 2 |
| CH₃ | H | H | H | CH₂CH(CH₃)₂ | H | CH₃ | 2 |
| CH₃ | H | CH₃ | H | H | H | CH₃ | 2 |
| CH₃ | H | OCH₃ | H | H | H | CH₃ | 2 |
| CH₃ | H | F | H | H | H | CH₃ | 2 |
| CH₃ | H | Cl | H | H | H | CH₃ | 2 |
| CH₃ | H | Br | H | H | H | CH₃ | 2 |
| CH₃ | H | H | H | H | CH₃ | CH₃ | 2 |
| CH₃ | H | H | H | H | OCH₃ | CH₃ | 2 |
| CH₃ | H | H | H | H | F | CH₃ | 2 |
| CH₃ | H | H | H | H | Cl | CH₃ | 2 |
| CH₃ | H | H | H | H | Br | CH₃ | 2 |
| H | CH₃ | H | H | H | H | CH₃ | 2 |
| H | CH₃ | H | H | H | H | CH₂CH₃ | 2 |
| H | CH₃ | H | H | H | H | CH₂CH₂CH₃ | 2 |
| H | CH₃ | H | H | H | H | CH(CH₃)₂ | 2 |
| H | CH₃ | H | H | H | H | CH₂CH=CH₂ | 2 |
| H | CH₃ | H | H | H | H | CH=CHCH₃ | 2 |
| H | CH₃ | H | H | H | H | CH₂CH=CHCH₃ | 2 |
| H | CH₃ | H | H | H | H | CH=CHCH₂CH₃ | 2 |
| H | CH₃ | H | H | H | H | CH₂-cyclopropyl | 2 |
| H | CH₃ | H | H | H | H | cyclopentyl | 2 |
| H | CH₂CH₃ | H | H | H | H | CH₂CH₂CH₃ | 2 |
| H | CH₂CH₂CH₃ | H | H | H | H | CH₂CH₂CH₃ | 2 |
| H | CH(CH₃)₂ | H | H | H | H | CH₂CH₂CH₃ | 2 |
| OCH₃ | H | H | H | H | H | CH₃ | 2 |
| OCH₃ | H | H | H | H | H | CH₂CH₃ | 2 |
| OCH₃ | H | H | H | H | H | CH₂CH₂CH₃ | 2 |
| OCH₃ | H | H | H | H | H | CH(CH₃)₂ | 2 |
| OCH₃ | H | H | H | H | H | CH₂CH=CH₂ | 2 |
| OCH₃ | H | H | H | H | H | CH=CHCH₃ | 2 |
| OCH₃ | H | H | H | H | H | CH₂CH=CHCH₃ | 2 |
| OCH₃ | H | H | H | H | H | CH=CHCH₂CH₃ | 2 |
| OCH₃ | H | H | H | H | H | CH₂-cyclopropyl | 2 |
| OCH₃ | H | H | H | H | H | cyclopentyl | 2 |
| CH₃ | CH₃ | H | H | H | H | CH₃ | 2 |
| CH₃ | CH₃ | H | H | H | H | CH₂CH₃ | 2 |
| CH₃ | CH₃ | H | H | H | H | CH₂CH₂CH₃ | 2 |
| CH₃ | CH₃ | H | H | H | H | CH(CH₃)₂ | 2 |
| CH₃ | CH₃ | H | H | H | H | CH=CHCH₃ | 2 |
| CH₃ | CH₃ | H | H | H | H | CH₂CH=CH₃ | 2 |
| CH₃ | CH₃ | H | H | H | H | CH=CHCH₂CH₃ | 2 |
| CH₃ | CH₃ | H | H | H | H | CH₂CH=CH₂CH₃ | 2 |
| CH₃ | CH₃ | H | H | H | H | CH₂-cyclopropyl | 2 |

TABLE I-B-continued

| R₁ | R₂ | R₅ | R₆ | R₇ | R₈ | R₉ | n |
|---|---|---|---|---|---|---|---|
| $CH_3$ | $CH_3$ | H | H | H | H | cyclopentyl | 2 |
| $CH_3$ | H | H | H | H | H | $(CH_2)_3CH_3$ | 0 |
| $CH_3$ | H | H | H | H | H | $(CH_2)_3CH_3$ | 1 |
| $CH_3$ | H | H | H | H | H | $(CH_2)_3CH_3$ | 2 |
| $C_2H_5$ | H | H | H | H | H | $(CH_2)_3CH_3$ | 0 |
| $C_2H_5$ | H | H | H | H | H | $(CH_2)_3CH_3$ | 1 |
| $C_2H_5$ | H | H | H | H | H | $(CH_2)_3CH_3$ | 2 |
| $CH_3CH_2CH_2$ | H | H | H | H | H | $(CH_2)_3CH_3$ | 0 |
| $CH_3CH_2CH_2$ | H | H | H | H | H | $(CH_2)_3CH_3$ | 1 |
| $CH_3CH_2CH_2$ | H | H | H | H | H | $(CH_2)_3CH_3$ | 2 |
| $(CH_3)_2CH$ | H | H | H | H | H | $(CH_2)_3CH_3$ | 2 |
| H | $CH_3$ | H | H | H | H | $(CH_2)_3CH_3$ | 2 |
| $CH_3$ | H | F | H | H | H | $(CH_2)_2CH_3$ | 2 |
| $CH_3$ | H | Cl | H | H | H | $(CH_2)_2CH_3$ | 2 |
| $CH_3$ | H | Br | H | H | H | $(CH_2)_2CH_3$ | 2 |
| $CH_3$ | H | $CH_3$ | H | H | H | $(CH_2)_2CH_3$ | 2 |
| $CH_3$ | H | $OCH_3$ | H | H | H | $(CH_2)_2CH_3$ | 2 |
| $CH_3$ | H | H | F | H | H | $(CH_2)_2CH_3$ | 2 |
| $CH_3$ | H | H | Cl | H | H | $(CH_2)_2CH_3$ | 2 |
| $CH_3$ | H | H | Br | H | H | $(CH_2)_2CH_3$ | 2 |
| $CH_3$ | H | H | $CH_3$ | H | H | $(CH_2)_2CH_3$ | 2 |
| $CH_3$ | H | H | $OCH_3$ | H | H | $(CH_2)_2CH_3$ | 2 |
| $CH_3$ | H | H | H | H | F | $(CH_2)_2CH_3$ | 2 |
| $CH_3$ | H | H | H | H | Cl | $(CH_2)_2CH_3$ | 2 |
| $CH_3$ | H | H | H | H | Br | $(CH_2)_2CH_3$ | 2 |
| $CH_3$ | H | H | H | H | $CH_3$ | $(CH_2)_2CH_3$ | 2 |
| $CH_3$ | H | H | H | H | $OCH_3$ | $(CH_2)_2CH_3$ | 2 |
| $CH_3$ | H | Cl | H | Cl | H | $(CH_2)_2CH_3$ | 2 |
| $CH_3$ | H | Cl | H | Cl | Cl | $(CH_2)_2CH_3$ | 2 |
| $CH_3$ | H | $CH_3$ | H | Cl | $CH_3$ | $(CH_2)_2CH_3$ | 2 |
| $CH_3$ | H | H | H | $SCH_3$ | H | $(CH_2)_2CH_3$ | 2 |
| $CH_3$ | H | H | H | $SCH_3$ | H | $(CH_2)_2CH_3$ | 2 |

TABLE I-C

| R₁ | R₂ | R₅ | R₆ | R₇ | R₈ | R₉ | n | m.p. (°C.) |
|---|---|---|---|---|---|---|---|---|
| $CH_3$ | H | H | H | H | H | $CH_3$ | 1 | |
| $CH_3$ | H | H | H | H | H | $CH_3$ | 2 | 191–193 |
| $CH_3$ | H | H | H | H | H | $CH_2CH_3$ | 1 | |
| $CH_3$ | H | H | H | H | H | $CH_2CH_3$ | 2 | |
| $CH_3$ | H | H | H | H | H | $CH_2CH_2CH_3$ | 0 | |
| $CH_3$ | H | H | H | H | H | $CH_2CH_2CH_3$ | 1 | |
| $CH_3$ | H | H | H | H | H | $CH_2CH_2CH_3$ | 2 | 174–176 |
| $CH_3$ | H | H | H | H | H | $CH(CH_3)_2$ | 0 | |
| $CH_3$ | H | H | H | H | H | $CH(CH_3)_2$ | 1 | |
| $CH_3$ | H | H | H | H | H | $CH(CH_3)_2$ | 2 | |
| $CH_3$ | H | H | H | H | H | $CH_2CH=CH_2$ | 0 | |
| $CH_3$ | H | H | H | H | H | $CH_2CH=CH_2$ | 1 | |
| $CH_3$ | H | H | H | H | H | $CH_2CH=CH_2$ | 2 | |
| $CH_3$ | H | H | H | H | H | $CH=CHCH_3$ | 0 | |
| $CH_3$ | H | H | H | H | H | $CH=CHCH_3$ | 1 | |
| $CH_3$ | H | H | H | H | H | $CH=CHCH_3$ | 2 | |

TABLE I-C-continued

[Structure: benzene ring with R5, R6, R7, R8 substituents, S(O)nR9 group, and SO2N(R2)C(O)N(R1)-pyrimidine with two OCH3 groups]

| R₁ | R₂ | R₅ | R₆ | R₇ | R₈ | R₉ | n | m.p. (°C.) |
|---|---|---|---|---|---|---|---|---|
| CH₃ | H | H | H | H | H | CH=CHCH₂CH₃ | 0 | |
| CH₃ | H | H | H | H | H | CH=CHCH₂CH₃ | 1 | |
| CH₃ | H | H | H | H | H | CH=CHCH₂CH₃ | 2 | |
| CH₃ | H | H | H | H | H | CH₂CH=CH₂CH₃ | 0 | |
| CH₃ | H | H | H | H | H | CH₂CH=CH₂CH₃ | 1 | |
| CH₃ | H | H | H | H | H | CH₂CH=CH₂CH₃ | 2 | |
| CH₃ | H | H | H | H | H | cyclopentyl | 0 | |
| CH₃ | H | H | H | H | H | cyclopentyl | 1 | |
| CH₃ | H | H | H | H | H | cyclopentyl | 2 | |
| CH₃ | H | H | H | H | H | CH₂-cyclopropyl | 0 | |
| CH₃ | H | H | H | H | H | CH₂-cyclopropyl | 1 | |
| CH₃ | H | H | H | H | H | CH₂-cyclopropyl | 2 | |
| CH₂CH₃ | H | H | H | H | H | CH₃ | 2 | |
| CH₂CH₂CH₃ | H | H | H | H | H | CH₃ | 2 | |
| CH(CH₃)₂ | H | H | H | H | H | CH₃ | 2 | |
| CH₂CH₃ | CH₃ | H | H | H | H | CH₃ | 2 | |
| CH₂CH₂CH₃ | CH₃ | H | H | H | H | CH₃ | 2 | |
| CH(CH₃)₂ | CH₃ | H | H | H | H | CH₃ | 2 | |
| CH₃ | CH₂CH₃ | H | H | H | H | CH₃ | 2 | |
| CH₃ | CH₂CH₂CH₃ | H | H | H | H | CH₃ | 2 | |
| CH₃ | CH(CH₃)₂ | H | H | H | H | CH₃ | 2 | |
| OCH₃ | CH₂CH₃ | H | H | H | H | CH₃ | 2 | |
| OCH₃ | CH₂CH₂CH₃ | H | H | H | H | CH₃ | 2 | |
| OCH₃ | CH(CH₃)₂ | H | H | H | H | CH₃ | 2 | |
| OCH₃ | CH₃ | H | H | H | H | CH₃ | 2 | |
| CH₃ | H | H | H | F | H | CH₃ | 2 | |
| CH₃ | H | H | H | Cl | H | CH₃ | 2 | |
| CH₃ | H | H | H | CH₃ | H | CH₃ | 2 | |
| CH₃ | H | H | H | OCH₃ | H | CH₃ | 2 | |
| CH₃ | H | H | H | CH₂CH₃ | H | CH₃ | 2 | |
| CH₃ | H | H | H | CH(CH₃)₂ | H | CH₃ | 2 | |
| CH₃ | H | H | H | CH₂CH₂CH₃ | H | CH₃ | 2 | |
| CH₃ | H | H | H | CH₂CH₂CH₂CH₃ | H | CH₃ | 2 | |
| CH₃ | H | H | H | CH₂CH(CH₃)₂ | H | CH₃ | 2 | |
| CH₃ | H | CH₃ | H | H | H | CH₃ | 2 | |
| CH₃ | H | OCH₃ | H | H | H | CH₃ | 2 | |
| CH₃ | H | F | H | H | H | CH₃ | 2 | |
| CH₃ | H | Cl | H | H | H | CH₃ | 2 | |
| CH₃ | H | Br | H | H | H | CH₃ | 2 | |
| CH₃ | H | H | H | H | CH₃ | CH₃ | 2 | |
| CH₃ | H | H | H | H | OCH₃ | CH₃ | 2 | |
| CH₃ | H | H | H | H | F | CH₃ | 2 | |
| CH₃ | H | H | H | H | Cl | CH₃ | 2 | |
| CH₃ | H | H | H | H | Br | CH₃ | 2 | |
| H | CH₃ | H | H | H | H | CH₃ | 2 | |

TABLE I-C-continued

[Structure diagram showing a benzene ring with substituents $R_5$, $R_6$, $R_7$, $R_8$, $S(O)_nR_9$, and $SO_2N(R_2)C(O)N(R_1)$– linked to a pyrimidine ring bearing two $OCH_3$ groups]

| $R_1$ | $R_2$ | $R_5$ | $R_6$ | $R_7$ | $R_8$ | $R_9$ | n | m.p. (°C.) |
|---|---|---|---|---|---|---|---|---|
| H | CH$_3$ | H | H | H | H | CH$_2$CH$_3$ | 2 | |
| H | CH$_3$ | H | H | H | H | CH$_2$CH$_2$CH$_3$ | 2 | |
| H | CH$_3$ | H | H | H | H | CH(CH$_3$)$_2$ | 2 | |
| H | CH$_3$ | H | H | H | H | CH$_2$CH=CH$_2$ | 2 | |
| H | CH$_3$ | H | H | H | H | CH=CHCH$_3$ | 2 | |
| H | CH$_3$ | H | H | H | H | CH$_2$CH=CHCH$_3$ | 2 | |
| H | CH$_3$ | H | H | H | H | CH=CHCH$_2$CH$_3$ | 2 | |
| H | CH$_3$ | H | H | H | H | CH$_2$-cyclopropyl | 2 | |
| H | CH$_3$ | H | H | H | H | cyclopentyl | 2 | |
| H | CH$_2$CH$_3$ | H | H | H | H | CH$_2$CH$_2$CH$_3$ | 2 | |
| H | CH$_2$CH$_2$CH$_3$ | H | H | H | H | CH$_2$CH$_2$CH$_3$ | 2 | |
| H | CH(CH$_3$)$_2$ | H | H | H | H | CH$_2$CH$_2$CH$_3$ | 2 | |
| OCH$_3$ | H | H | H | H | H | CH$_3$ | 2 | |
| OCH$_3$ | H | H | H | H | H | CH$_2$CH$_3$ | 2 | |
| OCH$_3$ | H | H | H | H | H | CH$_2$CH$_2$CH$_3$ | 2 | |
| OCH$_3$ | H | H | H | H | H | CH(CH$_3$)$_2$ | 2 | |
| OCH$_3$ | H | H | H | H | H | CH$_2$CH=CH$_2$ | 2 | |
| OCH$_3$ | H | H | H | H | H | CH=CHCH$_3$ | 2 | |
| OCH$_3$ | H | H | H | H | H | CH$_2$CH=CHCH$_3$ | 2 | |
| OCH$_3$ | H | H | H | H | H | CH=CHCH$_2$CH$_3$ | 2 | |
| OCH$_3$ | H | H | H | H | H | CH$_2$-cyclopropyl | 2 | |
| OCH$_3$ | H | H | H | H | H | cyclopentyl | 2 | |
| CH$_3$ | CH$_3$ | H | H | H | H | CH$_3$ | 2 | |
| CH$_3$ | CH$_3$ | H | H | H | H | CH$_2$CH$_3$ | 2 | |
| CH$_3$ | CH$_3$ | H | H | H | H | CH$_2$CH$_2$CH$_3$ | 2 | |
| CH$_3$ | CH$_3$ | H | H | H | H | CH(CH$_3$)$_2$ | 2 | |
| CH$_3$ | CH$_3$ | H | H | H | H | CH=CHCH$_3$ | 2 | |
| CH$_3$ | CH$_3$ | H | H | H | H | CH$_2$CH=CH$_3$ | 2 | |
| CH$_3$ | CH$_3$ | H | H | H | H | CH=CHCH$_2$CH$_3$ | 2 | |
| CH$_3$ | CH$_3$ | H | H | H | H | CH$_2$CH=CH$_2$CH$_3$ | 2 | |
| CH$_3$ | CH$_3$ | H | H | H | H | CH$_2$-cyclopropyl | 2 | |
| CH$_3$ | CH$_3$ | H | H | H | H | cyclopentyl | 2 | |
| CH$_3$ | H | H | H | H | H | (CH$_2$)$_3$CH$_3$ | 0 | |
| CH$_3$ | H | H | H | H | H | (CH$_2$)$_3$CH$_3$ | 1 | |
| CH$_3$ | H | H | H | H | H | (CH$_2$)$_3$CH$_3$ | 2 | |
| C$_2$H$_5$ | H | H | H | H | H | (CH$_2$)$_3$CH$_3$ | 0 | |
| C$_2$H$_5$ | H | H | H | H | H | (CH$_2$)$_3$CH$_3$ | 1 | |
| C$_2$H$_5$ | H | H | H | H | H | (CH$_2$)$_3$CH$_3$ | 2 | |
| CH$_3$CH$_2$CH$_2$ | H | H | H | H | H | (CH$_2$)$_3$CH$_3$ | 0 | |
| CH$_3$CH$_2$CH$_2$ | H | H | H | H | H | (CH$_2$)$_3$CH$_3$ | 1 | |
| CH$_3$CH$_2$CH$_2$ | H | H | H | H | H | (CH$_2$)$_3$CH$_3$ | 2 | |
| (CH$_3$)$_2$CH | H | H | H | H | H | (CH$_2$)$_3$CH$_3$ | 2 | |
| H | CH$_3$ | H | H | H | H | (CH$_2$)$_3$CH$_3$ | 2 | |

TABLE I-C-continued

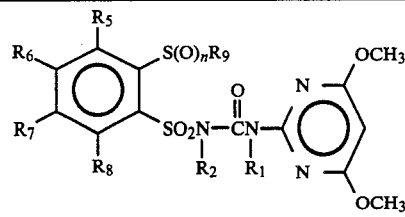

| R₁ | R₂ | R₅ | R₆ | R₇ | R₈ | R₉ | n | m.p. (°C.) |
|---|---|---|---|---|---|---|---|---|
| CH₃ | H | F | H | H | H | (CH₃)₂CH₃ | 2 | |
| CH₃ | H | Cl | H | H | H | (CH₂)₂CH₃ | 2 | |
| CH₃ | H | Br | H | H | H | (CH₂)₂CH₃ | 2 | |
| CH₃ | H | CH₃ | H | H | H | (CH₂)₂CH₃ | 2 | |
| CH₃ | H | OCH₃ | H | H | H | (CH₂)₂CH₃ | 2 | |
| CH₃ | H | H | F | H | H | (CH₂)₂CH₃ | 2 | |
| CH₃ | H | H | Cl | H | H | (CH₂)₂CH₃ | 2 | |
| CH₃ | H | H | Br | H | H | (CH₂)₂CH₃ | 2 | |
| CH₃ | H | H | CH₃ | H | H | (CH₂)₂CH₃ | 2 | |
| CH₃ | H | H | OCH₃ | H | H | (CH₂)₂CH₃ | 2 | |
| CH₃ | H | H | H | H | F | (CH₂)₂CH₃ | 2 | |
| CH₃ | H | H | H | H | Cl | (CH₂)₂CH₃ | 2 | |
| CH₃ | H | H | H | H | Br | (CH₂)₂CH₃ | 2 | |
| CH₃ | H | H | H | H | CH₃ | (CH₂)₂CH₃ | 2 | |
| CH₃ | H | H | H | H | OCH₃ | (CH₂)₂CH₃ | 2 | |
| CH₃ | H | Cl | Cl | H | H | (CH₂)₂CH₃ | 2 | |
| CH₃ | H | Cl | H | Cl | Cl | (CH₂)₂CH₃ | 2 | |
| CH₃ | H | CH₃ | H | CH₃ | CH₃ | (CH₂)₂CH₃ | 2 | |
| CH₃ | H | H | H | SCH₃ | H | (CH₂)₂CH₃ | 2 | |
| CH₃ | H | H | H | SC₂H₅ | H | (CH₂)₂CH₃ | 2 | |

TABLE I-D

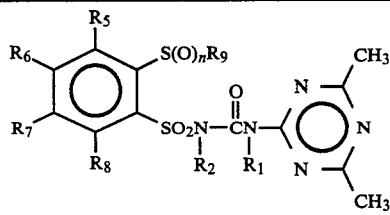

| R₁ | R₂ | R₅ | R₆ | R₇ | R₈ | R₉ | n |
|---|---|---|---|---|---|---|---|
| CH₃ | H | H | H | H | H | CH₃ | 1 |
| CH₃ | H | H | H | H | H | CH₃ | 2 |
| CH₃ | H | H | H | H | H | CH₂CH₃ | 1 |
| CH₃ | H | H | H | H | H | CH₂CH₃ | 2 |
| CH₃ | H | H | H | H | H | CH₂CH₂CH₃ | 0 |
| CH₃ | H | H | H | H | H | CH₂CH₂CH₃ | 1 |
| CH₃ | H | H | H | H | H | CH₂CH₂CH₃ | 2 |
| CH₃ | H | H | H | H | H | CH(CH₃)₂ | 0 |
| CH₃ | H | H | H | H | H | CH(CH₃)₂ | 1 |
| CH₃ | H | H | H | H | H | CH(CH₃)₂ | 2 |
| CH₃ | H | H | H | H | H | CH₂CH=CH₂ | 0 |
| CH₃ | H | H | H | H | H | CH₂CH=CH₂ | 1 |
| CH₃ | H | H | H | H | H | CH₂CH=CH₂ | 2 |
| CH₃ | H | H | H | H | H | CH=CHCH₃ | 0 |
| CH₃ | H | H | H | H | H | CH=CHCH₃ | 1 |
| CH₃ | H | H | H | H | H | CH=CHCH₃ | 2 |
| CH₃ | H | H | H | H | H | CH=CHCH₂CH₃ | 0 |
| CH₃ | H | H | H | H | H | CH=CHCH₂CH₃ | 1 |
| CH₃ | H | H | H | H | H | CH=CHCH₂CH₃ | 2 |
| CH₃ | H | H | H | H | H | CH₂CH=CH₂CH₃ | 0 |
| CH₃ | H | H | H | H | H | CH₂CH=CH₂CH₃ | 1 |
| CH₃ | H | H | H | H | H | CH₂CH=CH₂CH₃ | 2 |
| CH₃ | H | H | H | H | H |  | 0 |

TABLE I-D-continued

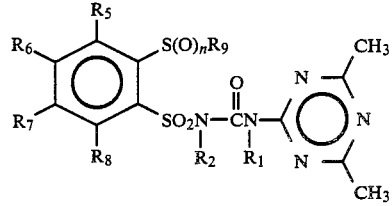

| R₁ | R₂ | R₅ | R₆ | R₇ | R₈ | R₉ | n |
|---|---|---|---|---|---|---|---|
| $CH_3$ | H | H | H | H | H |  | 1 |
| $CH_3$ | H | H | H | H | H |  | 2 |
| $CH_3$ | H | H | H | H | H |  | 0 |
| $CH_3$ | H | H | H | H | H |  | 1 |
| $CH_3$ | H | H | H | H | H |  | 2 |
| $CH_2CH_3$ | H | H | H | H | H | $CH_3$ | 2 |
| $CH_2CH_2CH_3$ | H | H | H | H | H | $CH_3$ | 2 |
| $CH(CH_3)_2$ | H | H | H | H | H | $CH_3$ | 2 |
| $CH_2CH_3$ | $CH_3$ | H | H | H | H | $CH_3$ | 2 |
| $CH_2CH_2CH_3$ | $CH_3$ | H | H | H | H | $CH_3$ | 2 |
| $CH(CH_3)_2$ | $CH_3$ | H | H | H | H | $CH_3$ | 2 |
| $CH_3$ | $CH_2CH_3$ | H | H | H | H | $CH_3$ | 2 |
| $CH_3$ | $CH_2CH_2CH_3$ | H | H | H | H | $CH_3$ | 2 |
| $CH_3$ | $CH(CH_3)_2$ | H | H | H | H | $CH_3$ | 2 |
| $OCH_3$ | $CH_2CH_3$ | H | H | H | H | $CH_3$ | 2 |
| $OCH_3$ | $CH_2CH_2CH_3$ | H | H | H | H | $CH_3$ | 2 |
| $OCH_3$ | $CH(CH_3)_2$ | H | H | H | H | $CH_3$ | 2 |
| $OCH_3$ | $CH_3$ | H | H | H | H | $CH_3$ | 2 |
| $CH_3$ | H | H | H | F | H | $CH_3$ | 2 |
| $CH_3$ | H | H | H | Cl | H | $CH_3$ | 2 |
| $CH_3$ | H | H | H | $CH_3$ | H | $CH_3$ | 2 |
| $CH_3$ | H | H | H | $OCH_3$ | H | $CH_3$ | 2 |
| $CH_3$ | H | H | H | $CH_2CH_3$ | H | $CH_3$ | 2 |
| $CH_3$ | H | H | H | $CH(CH_3)_2$ | H | $CH_3$ | 2 |
| $CH_3$ | H | H | H | $CH_2CH_2CH_3$ | H | $CH_3$ | 2 |
| $CH_3$ | H | H | H | $CH_2CH_2CH_2CH_3$ | H | $CH_3$ | 2 |
| $CH_3$ | H | H | H | $CH_2CH(CH_3)_2$ | H | $CH_3$ | 2 |
| $CH_3$ | H | $CH_3$ | H | H | H | $CH_3$ | 2 |
| $CH_3$ | H | $OCH_3$ | H | H | H | $CH_3$ | 2 |
| $CH_3$ | H | F | H | H | H | $CH_3$ | 2 |
| $CH_3$ | H | Cl | H | H | H | $CH_3$ | 2 |
| $CH_3$ | H | Br | H | H | H | $CH_3$ | 2 |
| $CH_3$ | H | H | H | H | $CH_3$ | $CH_3$ | 2 |
| $CH_3$ | H | H | H | H | $OCH_3$ | $CH_3$ | 2 |
| $CH_3$ | H | H | H | H | F | $CH_3$ | 2 |
| $CH_3$ | H | H | H | H | Cl | $CH_3$ | 2 |
| $CH_3$ | H | H | H | H | Br | $CH_3$ | 2 |
| H | $CH_3$ | H | H | H | H | $CH_3$ | 2 |
| H | $CH_3$ | H | H | H | H | $CH_2CH_3$ | 2 |
| H | $CH_3$ | H | H | H | H | $CH_2CH_2CH_3$ | 2 |
| H | $CH_3$ | H | H | H | H | $CH(CH_3)_2$ | 2 |
| H | $CH_3$ | H | H | H | H | $CH_2CH=CH_2$ | 2 |
| H | $CH_3$ | H | H | H | H | $CH=CHCH_3$ | 2 |
| H | $CH_3$ | H | H | H | H | $CH_2CH=CHCH_3$ | 2 |
| H | $CH_3$ | H | H | H | H | $CH=CHCH_2CH_3$ | 2 |
| H | $CH_3$ | H | H | H | H |  | 2 |

TABLE I-D-continued

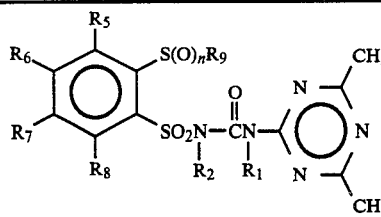

| R1 | R2 | R5 | R6 | R7 | R8 | R9 | n |
|---|---|---|---|---|---|---|---|
| H | CH3 | H | H | H | H |  | 2 |
| H | CH2CH3 | H | H | H | H | CH2CH2CH3 | 2 |
| H | CH2CH2CH3 | H | H | H | H | CH2CH2CH3 | 2 |
| H | CH(CH3)2 | H | H | H | H | CH2CH2CH3 | 2 |
| OCH3 | H | H | H | H | H | CH3 | 2 |
| OCH3 | H | H | H | H | H | CH2CH3 | 2 |
| OCH3 | H | H | H | H | H | CH2CH2CH3 | 2 |
| OCH3 | H | H | H | H | H | CH(CH3)2 | 2 |
| OCH3 | H | H | H | H | H | CH2CH=CH2 | 2 |
| OCH3 | H | H | H | H | H | CH=CHCH3 | 2 |
| OCH3 | H | H | H | H | H | CH2CH=CHCH3 | 2 |
| OCH3 | H | H | H | H | H | CH=CHCH2CH3 | 2 |
| OCH3 | H | H | H | H | H | 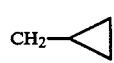 | 2 |
| OCH3 | H | H | H | H | H | 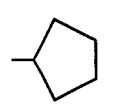 | 2 |
| CH3 | CH3 | H | H | H | H | CH3 | 2 |
| CH3 | CH3 | H | H | H | H | CH2CH3 | 2 |
| CH3 | CH3 | H | H | H | H | CH2CH2CH3 | 2 |
| CH3 | CH3 | H | H | H | H | CH(CH3)2 | 2 |
| CH3 | CH3 | H | H | H | H | CH=CHCH3 | 2 |
| CH3 | CH3 | H | H | H | H | CH2CH=CH3 | 2 |
| CH3 | CH3 | H | H | H | H | CH=CHCH2CH3 | 2 |
| CH3 | CH3 | H | H | H | H | CH2CH=CH2CH3 | 2 |
| CH3 | CH3 | H | H | H | H | 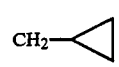 | 2 |
| CH3 | CH3 | H | H | H | H | 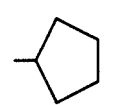 | 2 |
| CH3 | H | H | H | H | H | (CH2)3CH3 | 0 |
| CH3 | H | H | H | H | H | (CH2)3CH3 | 1 |
| CH3 | H | H | H | H | H | (CH2)3CH3 | 2 |
| C2H5 | H | H | H | H | H | (CH2)3CH3 | 0 |
| C2H5 | H | H | H | H | H | (CH2)3CH3 | 1 |
| C2H5 | H | H | H | H | H | (CH2)3CH3 | 2 |
| CH3CH2CH2 | H | H | H | H | H | (CH2)3CH3 | 0 |
| CH3CH2CH2 | H | H | H | H | H | (CH2)3CH3 | 1 |
| (CH3)2CH | H | H | H | H | H | (CH2)3CH3 | 2 |
| (CH3)2CH | H | H | H | H | H | (CH2)3CH3 | 2 |
| H | CH3 | H | H | H | H | (CH2)3CH3 | 2 |
| CH3 | H | F | H | H | H | (CH3)2CH3 | 2 |
| CH3 | H | Cl | H | H | H | (CH2)2CH3 | 2 |
| CH3 | H | Br | H | H | H | (CH2)2CH3 | 2 |
| CH3 | H | CH3 | H | H | H | (CH2)2CH3 | 2 |
| CH3 | H | OCH3 | H | H | H | (CH2)2CH3 | 2 |
| CH3 | H | H | F | H | H | (CH2)2CH3 | 2 |
| CH3 | H | H | Cl | H | H | (CH2)2CH3 | 2 |
| CH3 | H | H | Br | H | H | (CH2)2CH3 | 2 |
| CH3 | H | H | CH3 | H | H | (CH2)2CH3 | 2 |
| CH3 | H | H | OCH3 | H | H | (CH2)2CH3 | 2 |
| CH3 | H | H | H | H | F | (CH2)2CH3 | 2 |
| CH3 | H | H | H | H | Cl | (CH2)2CH3 | 2 |

TABLE I-D-continued

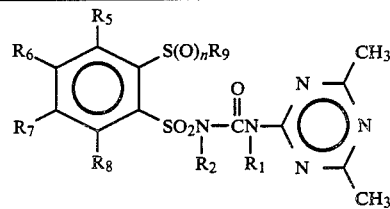

| $R_1$ | $R_2$ | $R_5$ | $R_6$ | $R_7$ | $R_8$ | $R_9$ | n |
|---|---|---|---|---|---|---|---|
| $CH_3$ | H | H | H | H | Br | $(CH_2)_2CH_3$ | 2 |
| $CH_3$ | H | H | H | H | $CH_3$ | $(CH_2)_2CH_3$ | 2 |
| $CH_3$ | H | H | H | H | $OCH_3$ | $(CH_2)_2CH_3$ | 2 |
| $CH_3$ | H | Cl | Cl | H | H | $(CH_2)_2CH_3$ | 2 |
| $CH_3$ | H | Cl | H | Cl | Cl | $(CH_2)_2CH_3$ | 2 |
| $CH_3$ | H | $CH_3$ | H | $CH_3$ | $CH_3$ | $(CH_2)_2CH_3$ | 2 |
| $CH_3$ | H | H | H | $SCH_3$ | H | $(CH_2)_2CH_3$ | 2 |
| $CH_3$ | H | H | H | $SC_2H_5$ | H | $(CH_2)_2CH_3$ | 2 |

TABLE I-E

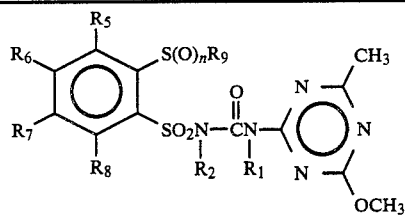

| $R_1$ | $R_2$ | $R_5$ | $R_6$ | $R_7$ | $R_8$ | $R_9$ | n | m.p. (°C.) |
|---|---|---|---|---|---|---|---|---|
| $CH_3$ | H | H | H | H | H | $CH_3$ | 1 | |
| $CH_3$ | H | H | H | H | H | $CH_3$ | 2 | 163–165 |
| $CH_3$ | H | H | H | H | H | $CH_2CH_3$ | 1 | |
| $CH_3$ | H | H | H | H | H | $CH_2CH_3$ | 2 | |
| $CH_3$ | H | H | H | H | H | $CH_2CH_2CH_3$ | 0 | |
| $CH_3$ | H | H | H | H | H | $CH_2CH_2CH_3$ | 1 | |
| $CH_3$ | H | H | H | H | H | $CH_2CH_2CH_3$ | 2 | 170–175 |
| $CH_3$ | H | H | H | H | H | $CH(CH_3)_2$ | 0 | |
| $CH_3$ | H | H | H | H | H | $CH(CH_3)_2$ | 1 | |
| $CH_3$ | H | H | H | H | H | $CH(CH_3)_2$ | 2 | |
| $CH_3$ | H | H | H | H | H | $CH_2CH=CH_2$ | 0 | |
| $CH_3$ | H | H | H | H | H | $CH_2CH=CH_2$ | 1 | |
| $CH_3$ | H | H | H | H | H | $CH_2CH=CH_2$ | 2 | |
| $CH_3$ | H | H | H | H | H | $CH=CHCH_3$ | 0 | |
| $CH_3$ | H | H | H | H | H | $CH=CHCH_3$ | 1 | |
| $CH_3$ | H | H | H | H | H | $CH=CHCH_3$ | 2 | |
| $CH_3$ | H | H | H | H | H | $CH=CHCH_2CH_3$ | 0 | |
| $CH_3$ | H | H | H | H | H | $CH=CHCH_2CH_3$ | 1 | |
| $CH_3$ | H | H | H | H | H | $CH=CHCH_2CH_3$ | 2 | |
| $CH_3$ | H | H | H | H | H | $CH_2CH=CH_2CH_3$ | 0 | |
| $CH_3$ | H | H | H | H | H | $CH_2CH=CH_2CH_3$ | 1 | |
| $CH_3$ | H | H | H | H | H | $CH_2CH=CH_2CH_3$ | 2 | |
| $CH_3$ | H | H | H | H | H | cyclopentyl | 0 | |
| $CH_3$ | H | H | H | H | H | cyclopentyl | 1 | |
| $CH_3$ | H | H | H | H | H | cyclopentyl | 2 | |
| $CH_3$ | H | H | H | H | H | $CH_2$-cyclopropyl | 0 | |

TABLE I-E-continued

[Structure: benzene ring with R5, R6, R7, R8 substituents and S(O)nR9 group, SO2N(R2)C(O)N(R1)- linked to a triazine bearing CH3 and OCH3]

| R₁ | R₂ | R₅ | R₆ | R₇ | R₈ | R₉ | n | m.p. (°C.) |
|---|---|---|---|---|---|---|---|---|
| CH₃ | H | H | H | H | H | CH₂-cyclopropyl | 1 | |
| CH₃ | H | H | H | H | H | CH₂-cyclopropyl | 2 | |
| CH₂CH₃ | H | H | H | H | H | CH₃ | 2 | |
| CH₂CH₂CH₃ | H | H | H | H | H | CH₃ | 2 | |
| CH(CH₃)₂ | H | H | H | H | H | CH₃ | 2 | |
| CH₂CH₃ | CH₃ | H | H | H | H | CH₃ | 2 | |
| CH₂CH₂CH₃ | CH₃ | H | H | H | H | CH₃ | 2 | |
| CH(CH₃)₂ | CH₃ | H | H | H | H | CH₃ | 2 | |
| CH₃ | CH₂CH₃ | H | H | H | H | CH₃ | 2 | |
| CH₃ | CH₂CH₂CH₃ | H | H | H | H | CH₃ | 2 | |
| CH₃ | CH(CH₃)₂ | H | H | H | H | CH₃ | 2 | |
| OCH₃ | CH₂CH₃ | H | H | H | H | CH₃ | 2 | |
| OCH₃ | CH₂CH₂CH₃ | H | H | H | H | CH₃ | 2 | |
| OCH₃ | CH(CH₃)₂ | H | H | H | H | CH₃ | 2 | |
| OCH₃ | CH₃ | H | H | H | H | CH₃ | 2 | |
| CH₃ | H | H | H | F | H | CH₃ | 2 | |
| CH₃ | H | H | H | Cl | H | CH₃ | 2 | |
| CH₃ | H | H | H | CH₃ | H | CH₃ | 2 | |
| CH₃ | H | H | H | OCH₃ | H | CH₃ | 2 | |
| CH₃ | H | H | H | CH₂CH₃ | H | CH₃ | 2 | |
| CH₃ | H | H | H | CH(CH₃)₂ | H | CH₃ | 2 | |
| CH₃ | H | H | H | CH₂CH₂CH₃ | H | CH₃ | 2 | |
| CH₃ | H | H | H | CH₂CH₂CH₂CH₃ | H | CH₃ | 2 | |
| CH₃ | H | H | H | CH₂CH(CH₃)₂ | H | CH₃ | 2 | |
| CH₃ | H | CH₃ | H | H | H | CH₃ | 2 | |
| CH₃ | H | OCH₃ | H | H | H | CH₃ | 2 | |
| CH₃ | H | F | H | H | H | CH₃ | 2 | |
| CH₃ | H | Cl | H | H | H | CH₃ | 2 | |
| CH₃ | H | Br | H | H | H | CH₃ | 2 | |
| CH₃ | H | H | H | H | CH₃ | CH₃ | 2 | |
| CH₃ | H | H | H | H | OCH₃ | CH₃ | 2 | |
| CH₃ | H | H | H | H | F | CH₃ | 2 | |
| CH₃ | H | H | H | H | Cl | CH₃ | 2 | |
| CH₃ | H | H | H | H | Br | CH₃ | 2 | |
| H | CH₃ | H | H | H | H | CH₃ | 2 | |
| H | CH₃ | H | H | H | H | CH₂CH₃ | 2 | |
| H | CH₃ | H | H | H | H | CH₂CH₂CH₃ | 2 | |
| H | CH₃ | H | H | H | H | CH(CH₃)₂ | 2 | |
| H | CH₃ | H | H | H | H | CH₂CH=CH₂ | 2 | |
| H | CH₃ | H | H | H | H | CH=CHCH₃ | 2 | |
| H | CH₃ | H | H | H | H | CH₂CH=CHCH₃ | 2 | |
| H | CH₃ | H | H | H | H | CH=CHCH₂CH₃ | 2 | |
| H | CH₃ | H | H | H | H | CH₂-cyclopropyl | 2 | |
| H | CH₃ | H | H | H | H | cyclopentyl | 2 | |
| H | CH₂CH₃ | H | H | H | H | CH₂CH₂CH₃ | 2 | |
| H | CH₂CH₂CH₃ | H | H | H | H | CH₂CH₂CH₃ | 2 | |
| H | CH(CH₃)₂ | H | H | H | H | CH₂CH₂CH₃ | 2 | |
| OCH₃ | H | H | H | H | H | CH₃ | 2 | |
| OCH₃ | H | H | H | H | H | CH₂CH₃ | 2 | |
| OCH₃ | H | H | H | H | H | CH₂CH₂CH₃ | 2 | |
| OCH₃ | H | H | H | H | H | CH(CH₃)₂ | 2 | |
| OCH₃ | H | H | H | H | H | CH₂CH=CH₂ | 2 | |
| OCH₃ | H | H | H | H | H | CH=CHCH₃ | 2 | |
| OCH₃ | H | H | H | H | H | CH₂CH=CHCH₃ | 2 | |
| OCH₃ | H | H | H | H | H | CH=CHCH₂CH₃ | 2 | |

TABLE I-E-continued

Structure: benzene ring with R5, R6, R7, R8 substituents, S(O)nR9 group, and SO2N(R2)-C(O)-N(R1)- linked to a pyrimidine (CH3, OCH3 substituents, N atoms).

| R1 | R2 | R5 | R6 | R7 | R8 | R9 | n | m.p. (°C.) |
|---|---|---|---|---|---|---|---|---|
| OCH3 | H | H | H | H | H | CH2—△ (cyclopropyl) | 2 | |
| OCH3 | H | H | H | H | H | cyclopentyl | 2 | |
| CH3 | CH3 | H | H | H | H | CH3 | 2 | |
| CH3 | CH3 | H | H | H | H | CH2CH3 | 2 | |
| CH3 | CH3 | H | H | H | H | CH2CH2CH3 | 2 | |
| CH3 | CH3 | H | H | H | H | CH(CH3)2 | 2 | |
| CH3 | CH3 | H | H | H | H | CH=CHCH3 | 2 | |
| CH3 | CH3 | H | H | H | H | CH2CH=CH3 | 2 | |
| CH3 | CH3 | H | H | H | H | CH=CHCH2CH3 | 2 | |
| CH3 | CH3 | H | H | H | H | CH2CH=CH2CH3 | 2 | |
| CH3 | CH3 | H | H | H | H | CH2—△ (cyclopropyl) | 2 | |
| CH3 | CH3 | H | H | H | H | cyclopentyl | 2 | |
| CH3 | H | H | H | H | H | (CH2)3CH3 | 0 | |
| CH3 | H | H | H | H | H | (CH2)3CH3 | 1 | |
| CH3 | H | H | H | H | H | (CH2)3CH3 | 2 | |
| C2H5 | H | H | H | H | H | (CH2)3CH3 | 0 | |
| C2H5 | H | H | H | H | H | (CH2)3CH3 | 1 | |
| C2H5 | H | H | H | H | H | (CH2)3CH3 | 2 | |
| CH3CH2CH2 | H | H | H | H | H | (CH2)3CH3 | 0 | |
| CH3CH2CH2 | H | H | H | H | H | (CH2)3CH3 | 1 | |
| CH3CH2CH2 | H | H | H | H | H | (CH2)3CH3 | 2 | |
| (CH3)2CH | H | H | H | H | H | (CH2)3CH3 | 2 | |
| H | CH3 | H | H | H | H | (CH2)3CH3 | 2 | |
| CH3 | H | F | H | H | H | (CH3)2CH3 | 2 | |
| CH3 | H | Cl | H | H | H | (CH2)2CH3 | 2 | |
| CH3 | H | Br | H | H | H | (CH2)2CH3 | 2 | |
| CH3 | H | CH3 | H | H | H | (CH2)2CH3 | 2 | |
| CH3 | H | OCH3 | H | H | H | (CH2)2CH3 | 2 | |
| CH3 | H | H | F | H | H | (CH2)2CH3 | 2 | |
| CH3 | H | H | Cl | H | H | (CH2)2CH3 | 2 | |
| CH3 | H | H | Br | H | H | (CH2)2CH3 | 2 | |
| CH3 | H | H | CH3 | H | H | (CH2)2CH3 | 2 | |
| CH3 | H | H | OCH3 | H | H | (CH2)2CH3 | 2 | |
| CH3 | H | H | H | H | F | (CH2)2CH3 | 2 | |
| CH3 | H | H | H | H | Cl | (CH2)2CH3 | 2 | |
| CH3 | H | H | H | H | Br | (CH2)2CH3 | 2 | |
| CH3 | H | H | H | H | CH3 | (CH2)2CH3 | 2 | |
| CH3 | H | H | H | H | OCH | (CH2)2CH3 | 2 | |
| CH3 | H | Cl | Cl | H | H | (CH2)2CH3 | 2 | |
| CH3 | H | Cl | H | Cl | Cl | (CH2)2CH3 | 2 | |
| CH3 | H | CH3 | H | CH3 | CH3 | (CH2)2CH3 | 2 | |
| CH3 | H | H | H | SCH3 | H | (CH2)2CH3 | 2 | |
| CH3 | H | H | H | SC2H5 | H | (CH2)2CH3 | 2 | |

TABLE I-F

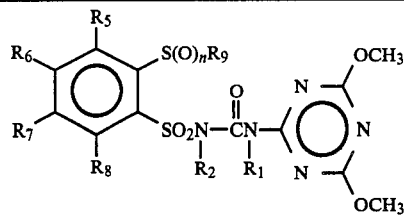

| R₁ | R₂ | R₅ | R₆ | R₇ | R₈ | R₉ | n | m.p. (°C.) |
|---|---|---|---|---|---|---|---|---|
| CH₃ | H | H | H | H | H | CH₃ | 1 | |
| CH₃ | H | H | H | H | H | CH₃ | 2 | 160–162 |
| CH₃ | H | H | H | H | H | CH₂CH₃ | 1 | |
| CH₃ | H | H | H | H | H | CH₂CH₃ | 2 | |
| CH₃ | H | H | H | H | H | CH₂CH₂CH₃ | 0 | |
| CH₃ | H | H | H | H | H | CH₂CH₂CH₃ | 1 | |
| CH₃ | H | H | H | H | H | CH₂CH₂CH₃ | 2 | 152–158 |
| CH₃ | H | H | H | H | H | CH(CH₃)₂ | 0 | |
| CH₃ | H | H | H | H | H | CH(CH₃)₂ | 1 | |
| CH₃ | H | H | H | H | H | CH(CH₃)₂ | 2 | 157–164 |
| CH₃ | H | H | H | H | H | CH₂CH=CH₂ | 0 | |
| CH₃ | H | H | H | H | H | CH₂CH=CH₂ | 1 | |
| CH₃ | H | H | H | H | H | CH₂CH=CH₂ | 2 | |
| CH₃ | H | H | H | H | H | CH=CHCH₃ | 0 | |
| CH₃ | H | H | H | H | H | CH=CHCH₃ | 1 | |
| CH₃ | H | H | H | H | H | CH=CHCH₃ | 2 | |
| CH₃ | H | H | H | H | H | CH=CHCH₂CH₃ | 0 | |
| CH₃ | H | H | H | H | H | CH=CHCH₂CH₃ | 1 | |
| CH₃ | H | H | H | H | H | CH=CHCH₂CH₃ | 2 | |
| CH₃ | H | H | H | H | H | CH₂CH=CH₂CH₃ | 0 | |
| CH₃ | H | H | H | H | H | CH₂CH=CH₂CH₃ | 1 | |
| CH₃ | H | H | H | H | H | CH₂CH=CH₂CH₃ | 2 | |
| CH₃ | H | H | H | H | H | cyclopentyl | 0 | |
| CH₃ | H | H | H | H | H | cyclopentyl | 1 | |
| CH₃ | H | H | H | H | H | cyclopentyl | 2 | |
| CH₃ | H | H | H | H | H | CH₂-cyclopropyl | 0 | |
| CH₃ | H | H | H | H | H | CH₂-cyclopropyl | 1 | |
| CH₃ | H | H | H | H | H | CH₂-cyclopropyl | 2 | |
| CH₂CH₃ | H | H | H | H | H | CH₃ | 2 | |
| CH₂CH₂CH₃ | H | H | H | H | H | CH₃ | 2 | |
| CH(CH₃)₂ | H | H | H | H | H | CH₃ | 2 | |
| CH₂CH₃ | CH₃ | H | H | H | H | CH₃ | 2 | |
| CH₂CH₂CH₃ | CH₃ | H | H | H | H | CH₃ | 2 | |
| CH(CH₃)₂ | CH₃ | H | H | H | H | CH₃ | 2 | |
| CH₃ | CH₂CH₃ | H | H | H | H | CH₃ | 2 | |
| CH₃ | CH₂CH₂CH₃ | H | H | H | H | CH₃ | 2 | |
| CH₃ | CH(CH₃)₂ | H | H | H | H | CH₃ | 2 | |
| OCH₃ | CH₂CH₃ | H | H | H | H | CH₃ | 2 | |
| OCH₃ | CH₂CH₂CH₃ | H | H | H | H | CH₃ | 2 | |
| OCH₃ | CH(CH₃)₂ | H | H | H | H | CH₃ | 2 | |
| OCH₃ | CH₃ | H | H | H | H | CH₃ | 2 | |
| CH₃ | H | H | H | F | H | CH₃ | 2 | |
| CH₃ | H | H | H | Cl | H | CH₃ | 2 | |
| CH₃ | H | H | H | CH₃ | H | CH₃ | 2 | |
| CH₃ | H | H | H | OCH₃ | H | CH₃ | 2 | |

TABLE I-F-continued

Structure: phenyl ring with R5, R6, R7, R8 substituents, S(O)nR9 group, SO2N(R2)C(O)N(R1)- linked to pyrimidine with two OCH3 groups

| R₁ | R₂ | R₅ | R₆ | R₇ | R₈ | R₉ | n | m.p. (°C.) |
|---|---|---|---|---|---|---|---|---|
| CH₃ | H | H | H | CH₂CH₃ | H | CH₃ | 2 | |
| CH₃ | H | H | H | CH(CH₃)₂ | H | CH₃ | 2 | |
| CH₃ | H | H | H | CH₂CH₂CH₃ | H | CH₃ | 2 | |
| CH₃ | H | H | H | CH₂CH₂CH₂CH₃ | H | CH₃ | 2 | |
| CH₃ | H | H | H | CH₂CH(CH₃)₂ | H | CH₃ | 2 | |
| CH₃ | H | CH₃ | H | H | H | CH₃ | 2 | |
| CH₃ | H | OCH₃ | H | H | H | CH₃ | 2 | |
| CH₃ | H | F | H | H | H | CH₃ | 2 | |
| CH₃ | H | Cl | H | H | H | CH₃ | 2 | |
| CH₃ | H | Br | H | H | H | CH₃ | 2 | |
| CH₃ | H | H | H | H | CH₃ | CH₃ | 2 | |
| CH₃ | H | H | H | H | OCH₃ | CH₃ | 2 | |
| CH₃ | H | H | H | H | F | CH₃ | 2 | |
| CH₃ | H | H | H | H | Cl | CH₃ | 2 | |
| CH₃ | H | H | H | H | Br | CH₃ | 2 | |
| H | CH₃ | H | H | H | H | CH₃ | 2 | |
| H | CH₃ | H | H | H | H | CH₂CH₃ | 2 | |
| H | CH₃ | H | H | H | H | CH₂CH₂CH₃ | 2 | |
| H | CH₃ | H | H | H | H | CH(CH₃)₂ | 2 | |
| H | CH₃ | H | H | H | H | CH₂CH=CH₂ | 2 | |
| H | CH₃ | H | H | H | H | CH=CHCH₃ | 2 | |
| H | CH₃ | H | H | H | H | CH₂CH=CHCH₃ | 2 | |
| H | CH₃ | H | H | H | H | CH=CHCH₂CH₃ | 2 | |
| H | CH₃ | H | H | H | H | CH₂-cyclopropyl | 2 | |
| H | CH₃ | H | H | H | H | cyclopentyl | 2 | |
| H | CH₂CH₃ | H | H | H | H | CH₂CH₂CH₃ | 2 | |
| H | CH₂CH₂CH₃ | H | H | H | H | CH₂CH₂CH₃ | 2 | |
| H | CH(CH₃)₂ | H | H | H | H | CH₂CH₂CH₃ | 2 | |
| OCH₃ | H | H | H | H | H | CH₃ | 2 | |
| OCH₃ | H | H | H | H | H | CH₂CH₃ | 2 | |
| OCH₃ | H | H | H | H | H | CH₂CH₂CH₃ | 2 | |
| OCH₃ | H | H | H | H | H | CH(CH₃)₂ | 2 | |
| OCH₃ | H | H | H | H | H | CH₂CH=CH₂ | 2 | |
| OCH₃ | H | H | H | H | H | CH=CHCH₃ | 2 | |
| OCH₃ | H | H | H | H | H | CH₂CH=CHCH₃ | 2 | |
| OCH₃ | H | H | H | H | H | CH=CHCH₂CH₃ | 2 | |
| OCH₃ | H | H | H | H | H | CH₂-cyclopropyl | 2 | |
| OCH₃ | H | H | H | H | H | cyclopentyl | 2 | |
| CH₃ | CH₃ | H | H | H | H | CH₃ | 2 | |
| CH₃ | CH₃ | H | H | H | H | CH₂CH₃ | 2 | |
| CH₃ | CH₃ | H | H | H | H | CH₂CH₂CH₃ | 2 | |
| CH₃ | CH₃ | H | H | H | H | CH(CH₃)₂ | 2 | |
| CH₃ | CH₃ | H | H | H | H | CH=CHCH₃ | 2 | |
| CH₃ | CH₃ | H | H | H | H | CH₂CH=CH₃ | 2 | |
| CH₃ | CH₃ | H | H | H | H | CH=CHCH₂CH₃ | 2 | |
| CH₃ | CH₃ | H | H | H | H | CH₂CH=CH₂CH₃ | 2 | |
| CH₃ | CH₃ | H | H | H | H | CH₂-cyclopropyl | 2 | |

TABLE I-F-continued

| $R_1$ | $R_2$ | $R_5$ | $R_6$ | $R_7$ | $R_8$ | $R_9$ | n | m.p. (°C.) |
|---|---|---|---|---|---|---|---|---|
| $CH_3$ | $CH_3$ | H | H | H | H | cyclopentyl | 2 | |
| $CH_3$ | H | H | H | H | H | $(CH_2)_3CH_3$ | 0 | |
| $CH_3$ | H | H | H | H | H | $(CH_2)_3CH_3$ | 1 | |
| $CH_3$ | H | H | H | H | H | $(CH_2)_3CH_3$ | 2 | |
| $C_2H_5$ | H | H | H | H | H | $(CH_2)_3CH_3$ | 0 | |
| $C_2H_5$ | H | H | H | H | H | $(CH_2)_3CH_3$ | 1 | |
| $C_2H_5$ | H | H | H | H | H | $(CH_2)_3CH_3$ | 2 | |
| $CH_3CH_2CH_2$ | H | H | H | H | H | $(CH_2)_3CH_3$ | 0 | |
| $CH_3CH_2CH_2$ | H | H | H | H | H | $(CH_2)_3CH_3$ | 1 | |
| $CH_3CH_2CH_2$ | H | H | H | H | H | $(CH_2)_3CH_3$ | 2 | |
| $(CH_3)_2CH$ | H | H | H | H | H | $(CH_2)_3CH_3$ | 2 | |
| H | $CH_3$ | H | H | H | H | $(CH_2)_3CH_3$ | 2 | |
| $CH_3$ | H | F | H | H | H | $(CH_2)_2CH_3$ | 2 | |
| $CH_3$ | H | Cl | H | H | H | $(CH_2)_2CH_3$ | 2 | |
| $CH_3$ | H | Br | H | H | H | $(CH_2)_2CH_3$ | 2 | |
| $CH_3$ | H | $CH_3$ | H | H | H | $(CH_2)_2CH_3$ | 2 | |
| $CH_3$ | H | $OCH_3$ | H | H | H | $(CH_2)_2CH_3$ | 2 | |
| $CH_3$ | H | H | F | H | H | $(CH_2)_2CH_3$ | 2 | |
| $CH_3$ | H | H | Cl | H | H | $(CH_2)_2CH_3$ | 2 | |
| $CH_3$ | H | H | Br | H | H | $(CH_2)_2CH_3$ | 2 | |
| $CH_3$ | H | H | $CH_3$ | H | H | $(CH_2)_2CH_3$ | 2 | |
| $CH_3$ | H | H | $OCH_3$ | H | H | $(CH_2)_2CH_3$ | 2 | |
| $CH_3$ | H | H | H | H | F | $(CH_2)_2CH_3$ | 2 | |
| $CH_3$ | H | H | H | H | Cl | $(CH_2)_2CH_3$ | 2 | |
| $CH_3$ | H | H | H | H | Br | $(CH_2)_2CH_3$ | 2 | |
| $CH_3$ | H | H | H | H | $CH_3$ | $(CH_2)_2CH_3$ | 2 | |
| $CH_3$ | H | H | H | H | $OCH_3$ | $(CH_2)_2CH_3$ | 2 | |
| $CH_3$ | H | Cl | Cl | H | H | $(CH_2)_2CH_3$ | 2 | |
| $CH_3$ | H | Cl | H | Cl | Cl | $(CH_2)_2CH_3$ | 2 | |
| $CH_3$ | H | $CH_3$ | H | $CH_3$ | $CH_3$ | $(CH_2)_2CH_3$ | 2 | |
| $CH_3$ | H | H | H | $SCH_3$ | H | $(CH_2)_2CH_3$ | 2 | |
| $CH_3$ | H | H | H | $SC_2H_5$ | H | $(CH_2)_2CH_3$ | 2 | |

TABLE II-A

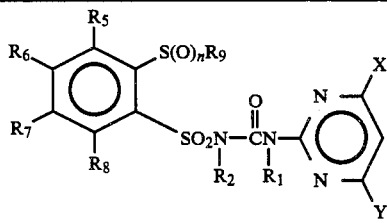

| $R_1$ | $R_2$ | $R_5$ | $R_6$ | $R_7$ | $R_8$ | $R_9$ | n | X | Y |
|---|---|---|---|---|---|---|---|---|---|
| $CH_3$ | H | H | H | H | H | $CH_3$ | 2 | $CH_2CH_3$ | $OCH_3$ |
| $CH_3$ | H | H | H | H | H | $CH_3$ | 2 | $OCH(CH_3)_2$ | $CH_3$ |
| $CH_3$ | H | H | H | H | H | $CH_3$ | 2 | $OCH_2CH_3$ | $OCH_3$ |
| $CH_3$ | H | H | H | H | H | $CH_3$ | 2 | $OCH_2CH_2CH_3$ | $CH_3$ |
| $CH_3$ | H | H | H | H | H | $CH_3$ | 2 | $CF_3$ | $OCH_3$ |
| $CH_3$ | H | H | H | H | H | $CH_3$ | 2 | $SCH_3$ | $CH_3$ |
| $CH_3$ | H | H | H | H | H | $CH_3$ | 2 | $CH_2OCH_3$ | $OCH_3$ |
| $CH_3$ | H | H | H | H | H | $CH_3$ | 2 | $O(CH_2)_2OCH_3$ | $CH_3$ |
| H | $CH_3$ | H | H | H | H | $CH_3$ | 2 | $CH_2CH_3$ | $CH_3$ |
| H | $CH_3$ | H | H | H | H | $CH_3$ | 2 | $OCH(CH_3)_2$ | $OCH_3$ |
| H | $CH_3$ | H | H | H | H | $CH_3$ | 2 | $OCH_2CH_3$ | $CH_3$ |
| H | $CH_3$ | H | H | H | H | $CH_3$ | 2 | $OCH_2CH_2CH_3$ | $OCH_3$ |
| H | $CH_3$ | H | H | H | H | $CH_3$ | 2 | $CF_3$ | $CH_3$ |
| H | $CH_3$ | H | H | H | H | $CH_3$ | 2 | $SCH_3$ | $OCH_3$ |
| H | $CH_3$ | H | H | H | H | $CH_3$ | 2 | $CH_2OCH_3$ | $CH_3$ |
| H | $CH_3$ | H | H | H | H | $CH_3$ | 2 | $O(CH_2)_2OCH_3$ | $OCH_3$ |

TABLE II-A-continued

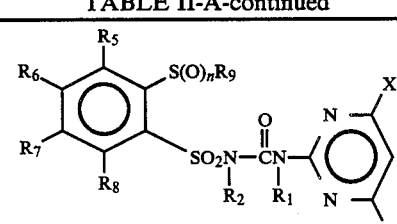

| $R_1$ | $R_2$ | $R_5$ | $R_6$ | $R_7$ | $R_8$ | $R_9$ | n | X | Y |
|---|---|---|---|---|---|---|---|---|---|
| $OCH_3$ | H | H | H | H | H | $CH_3$ | 2 | $CH_2CH_3$ | $OCH_3$ |
| $OCH_3$ | H | H | H | H | H | $CH_3$ | 2 | $OCH(CH_3)_2$ | $CH_3$ |
| $OCH_3$ | H | H | H | H | H | $CH_3$ | 2 | $OCH_2CH_3$ | $OCH_3$ |
| $OCH_3$ | H | H | H | H | H | $CH_3$ | 2 | $CF_3$ | $CH_3$ |
| $OCH_3$ | H | H | H | H | H | $CH_3$ | 2 | $SCH_3$ | $OCH_3$ |
| $OCH_3$ | H | H | H | H | H | $CH_3$ | 2 | $CH_2OCH_3$ | $CH_3$ |
| $OCH_3$ | H | H | H | H | H | $CH_3$ | 2 | $OCH_2CH_2CH_3$ | $OCH_3$ |
| $OCH_3$ | H | H | H | H | H | $CH_3$ | 2 | $O(CH_2)_2OCH_3$ | $CH_3$ |
| $CH_3$ | $CH_3$ | H | H | H | H | $CH_3$ | 2 | $CH_2CH_3$ | $CH_3$ |
| $CH_3$ | $CH_3$ | H | H | H | H | $CH_3$ | 2 | $OCH(CH_3)_2$ | $OCH_3$ |
| $CH_3$ | $CH_3$ | H | H | H | H | $CH_3$ | 2 | $OCH_2CH_3$ | $CH_3$ |
| $CH_3$ | $CH_3$ | H | H | H | H | $CH_3$ | 2 | $OCH_2CH_2CH_3$ | $OCH_3$ |
| $CH_3$ | $CH_3$ | H | H | H | H | $CH_3$ | 2 | $CF_3$ | $CH_3$ |
| $CH_3$ | $CH_3$ | H | H | H | H | $CH_3$ | 2 | $SCH_3$ | $OCH_3$ |
| $CH_3$ | $CH_3$ | H | H | H | H | $CH_3$ | 2 | $CH_2OCH_3$ | $CH_3$ |

TABLE II-A-continued $R_5$, $R_6$, $R_7$, $R_8$ on benzene ring with $S(O)_nR_9$; $SO_2N(R_2)-C(O)-N(R_1)-$ pyrimidine with X, Y substituents.

| $R_1$ | $R_2$ | $R_5$ | $R_6$ | $R_7$ | $R_8$ | $R_9$ | n | X | Y |
|---|---|---|---|---|---|---|---|---|---|
| $CH_3$ | $CH_3$ | H | H | H | H | $CH_3$ | 2 | $OCH_2CH_2OCH_3$ | $OCH_3$ |

TABLE II-B $R_5$, $R_6$, $R_7$, $R_8$ on benzene ring with $S(O)_nR_9$; $SO_2N(R_2)-C(O)-N(R_1)-$ triazine with X, Y substituents.

| $R_1$ | $R_2$ | $R_5$ | $R_6$ | $R_7$ | $R_8$ | $R_9$ | n | X | Y |
|---|---|---|---|---|---|---|---|---|---|
| $CH_3$ | H | H | H | H | H | $CH_3$ | 2 | $CH_2CH_3$ | $OCH_3$ |
| $CH_3$ | H | H | H | H | H | $CH_3$ | 2 | $OCH(CH_3)_2$ | $CH_3$ |
| $CH_3$ | H | H | H | H | H | $CH_3$ | 2 | $OCH_2CH_3$ | $OCH_3$ |
| $CH_3$ | H | H | H | H | H | $CH_3$ | 2 | $OCH_2CH_2CH_3$ | $CH_3$ |
| $CH_3$ | H | H | H | H | H | $CH_3$ | 2 | $CF_2$ | $OCH_3$ |
| $CH_3$ | H | H | H | H | H | $CH_3$ | 2 | $SCH_3$ | $CH_3$ |
| $CH_3$ | H | H | H | H | H | $CH_3$ | 2 | $CH_2OCH_3$ | $OCH_3$ |
| $CH_3$ | H | H | H | H | H | $CH_3$ | 2 | $O(CH_2)_2OCH_3$ | $CH_3$ |
| H | $CH_3$ | H | H | H | H | $CH_3$ | 2 | $CH_2CH_3$ | $CH_3$ |
| H | $CH_3$ | H | H | H | H | $CH_3$ | 2 | $OCH(CH_3)_2$ | $OCH_3$ |
| H | $CH_3$ | H | H | H | H | $CH_3$ | 2 | $OCH_2CH_3$ | $CH_3$ |
| H | $CH_3$ | H | H | H | H | $CH_3$ | 2 | $OCH_2CH_2CH_3$ | $OCH_3$ |
| H | $CH_3$ | H | H | H | H | $CH_3$ | 2 | $CF_3$ | $CH_3$ |
| H | $CH_3$ | H | H | H | H | $CH_3$ | 2 | $SCH_3$ | $OCH_3$ |
| H | $CH_3$ | H | H | H | H | $CH_3$ | 2 | $CH_2OCH_3$ | $CH_3$ |
| H | $CH_3$ | H | H | H | H | $CH_3$ | 2 | $O(CH_2)_2OCH_3$ | $OCH_3$ |
| $OCH_3$ | H | H | H | H | H | $CH_3$ | 2 | $CH_2CH_3$ | $OCH_3$ |
| $OCH_3$ | H | H | H | H | H | $CH_3$ | 2 | $OCH(CH_3)_2$ | $CH_3$ |
| $OCH_3$ | H | H | H | H | H | $CH_3$ | 2 | $OCH_2CH_3$ | $OCH_3$ |
| $OCH_3$ | H | H | H | H | H | $CH_3$ | 2 | $CF_3$ | $CH_3$ |
| $OCH_3$ | H | H | H | H | H | $CH_3$ | 2 | $SCH_3$ | $OCH_3$ |
| $OCH_3$ | H | H | H | H | H | $CH_3$ | 2 | $CH_2OCH_3$ | $CH_3$ |
| $OCH_3$ | H | H | H | H | H | $CH_3$ | 2 | $OCH_2CH_2CH_3$ | $OCH_3$ |
| $OCH_3$ | H | H | H | H | H | $CH_3$ | 2 | $O(CH_2)_2OCH_3$ | $CH_3$ |
| $CH_3$ | $CH_3$ | H | H | H | H | $CH_3$ | 2 | $CH_2CH_3$ | $CH_3$ |
| $CH_3$ | $CH_3$ | H | H | H | H | $CH_3$ | 2 | $OCH(CH_3)_2$ | $OCH_3$ |
| $CH_3$ | $CH_3$ | H | H | H | H | $CH_3$ | 2 | $OCH_2CH_3$ | $CH_3$ |
| $CH_3$ | $CH_3$ | H | H | H | H | $CH_3$ | 2 | $OCH_2CH_2CH_3$ | $OCH_3$ |
| $CH_3$ | $CH_3$ | H | H | H | H | $CH_3$ | 2 | $CF_3$ | $CH_3$ |
| $CH_3$ | $CH_3$ | H | H | H | H | $CH_3$ | 2 | $SCH_3$ | $OCH_3$ |
| $CH_3$ | $CH_3$ | H | H | H | H | $CH_3$ | 2 | $CH_2OCH_3$ | $CH_3$ |
| $CH_3$ | $CH_3$ | H | H | H | H | $CH_3$ | 2 | $OCH_2CH_2OCH_3$ | $OCH_3$ |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE III

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Patent 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 3

Wettable Powder

N-[(4,6-dimethoxypyrimidin-2-yl)(methyl)aminocarbonyl]-2-(methylsulfonyl)benzenesulfonamide: 80%
sodium alkylnaphthalenesulfonate: 2%
sodium ligninsulfonate: 2%
synthetic amorphous silica: 3%
kaolinite: 13%

The ingredients are blended, hammer-milled until all the solids are essentially under 50 microns, reblended, and packaged.

EXAMPLE 4

Wettable Powder

N-[(4,6-dimethoxypyrimidin-2-yl)(methyl)aminocarbonyl]-2-(propylsulfonyl)benzenesulfonamide: 50%
sodium alkylnaphthalenesulfonate: 2%
low viscosity methyl cellulose: 2%
diatomaceous earth: 46%

The ingredients are blended, coarsely hammer-milled and then air-milled to produce particles essentially all below 10 microns in diameter. The product is reblended before packaging.

EXAMPLE 5

Granule

Wettable Powder of Example 4: 5%
attapulgite granules (U.S.S. 20-40 mesh; 0.84-0.42 mm): 95%

A slurry of wettable powder containing 25% solids is sprayed on the surface of attapulgite granules in a double-cone blender. The granules are dried and packaged.

EXAMPLE 6

Extruded Pellet

N-[(4,6-dimethoxy-1,3,5-triazin-2-yl)(methyl)aminocarbonyl]-2-(methylsulfonyl)benzenesulfonamide: 25%
anhydrous sodium sulfate: 10%
crude calcium ligninsulfonate: 5%
sodium alkylnaphthalenesulfonate: 1%
calcium/magnesium bentonite: 59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 7

Oil Suspension

N-[(4-methyl-6-methoxy-1,3,5-triazin-2-yl)(methyl)aminocarbonyl]-2-(methylsulfonyl)benzenesulfonamide: 25%
polyoxyethylene sorbitol hexaoleate: 5%
highly aliphatic hydrocarbon oil: 70%

The ingredients are ground together in a sand mill until the solid particles have been reduced to under about 5 microns. The resulting thick suspension may be applied directly, but preferably after being extended with oils or emulsified in water.

EXAMPLE 8

Wettable Powder

N-[(4,6-dimethoxy-1,3,5-triazin-2-yl)(methyl)aminocarbonyl]-2-(methylsulfonyl)benzenesulfonamide: 20%
sodium alkylnaphthalenesulfonate: 4%
sodium ligninsulfonate: 4%
low viscosity methyl cellulose: 3%
attapulgite: 69%

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 9

Low Strength Granule

N-[(4,6-dimethoxy-1,3,5-triazin-2-yl)(methyl)aminocarbonyl]-2-(propylsulfonyl)benzenesulfonamide: 1%
N,N-dimethylformamide: 9%
attapulgite granules (U.S.S. 20-40 sieve): 90%

The active ingredient is dissolved in the solvent and the solution is sprayed upon dedusted granules in a double cone blender. After spraying of the solution has been completed, the blender is allowed to run for a short period and then the granules are packaged.

EXAMPLE 10

Aqueous Suspension

N-[(4-methoxy-6-methyl-1,3,5-triazin-2-yl)(methyl)aminocarbonyl]-2-(propylsulfonyl)benzenesulfonamide: 40%
polyacrylic acid thickener: 0.3%
dodecylphenol polyethylene glycol ether: 0.5%
disodium phosphate: 1%
monosodium phosphate: 0.5%
polyvinyl alcohol: 1.0%
water: 56.7%

The ingredients are blended and ground together in a sand mill to produce particles essentially all under 5 microns in size.

EXAMPLE 11

Solution

N-[(4-methoxy-6-methyl-1,3,5-triazin-2-yl)(methyl)aminocarbonyl]-2-(propylsulfonyl)benzenesulfonamide, sodium salt: 5%
water: 95%

The salt is added directly to the water with stirring to produce the solution, which may then be packaged for use.

EXAMPLE 12

Low Strength Granule

N-[(4-methyl-6-methoxy-1,3,5-triazin-2-yl)(methyl)aminocarbonyl]-2-(methylsulfonyl)benzenesulfonamide: 0.1%
attapulgite granules (U.S.S. 20-40 mesh): 99.9%

The active ingredient is dissolved in a solvent and the solution is sprayed upon dedusted granules in a double-cone blender. After spraying of the solution has been completed, the material is warmed to evaporate the

EXAMPLE 13

Granule

N-[(4,6-dimethoxypyrimidin-2-yl)(methyl)aminocarbonyl]-2-(propylsulfonyl)benzenesulfonamide: 80%
wetting agent: 1%
crude ligninsulfonate salt (containing 5-20% of the natural sugars): 10%
attapulgite clay: 9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 14

High Strength Concentrate

N-[(4,6-dimethoxypyrimidin-2-yl)(methyl)aminocarbonyl]-2-(methylsulfonyl)benzenesulfonamide: 99%
silica aerogel: 0.5%
synthetic amorphous silica: 0.5%

The ingredients are blended and ground in a hammer-mill to produce a material essentially all passing a U.S.S. No. 50 screen (0.3 mm opening). The concentrate may be formulated further if necessary.

EXAMPLE 15

Wettable Powder

N-[(4,6-dimethoxy-1,3,5-triazin-2-yl)(methyl)aminocarbonyl]-2-(methylsulfonyl)benzenesulfonamide: 90%
dioctyl sodium sulfosuccinate: 0.1%
synthetic fine silica: 9.9%

The ingredients are blended and ground in a hammer-mill to produce particles essentially all below 100 microns. The material is sifted through a U.S.S. No. 50 screen and then packaged.

EXAMPLE 16

Wettable Powder

N-[(4-methoxy-6-methyl-1,3,5-triazin-2-yl)(methyl)aminocarbonyl]-2-(propylsulfonyl)benzenesulfonamide: 40%
sodium ligninsulfonate: 20%
montmorillonite clay: 40%

The ingredients are thoroughly blended, coarsely hammer-milled and then air-milled to produce particles essentially all below 10 microns in size. The material is reblended and then packaged.

EXAMPLE 17

Oil Suspension

N-[(4,6-dimethoxy-1,3,5-triazin-2-yl)(methyl)aminocarbonyl]-2-(methylsulfonyl)benzenesulfonamide: 35%
blend of polyalcohol carboxylic esters and oil soluble petroleum sulfonates: 6%
xylene: 59%

The ingredients are combined and ground together in a sand mill to produce particles essentially all below 5 microns. The product can be used directly, extended with oils, or emulsified in water.

EXAMPLE 18

Dust

N-[(4-methoxy-6-methyl-1,3,5-triazin-2-yl)(methyl)aminocarbonyl]-2-(propysulfonyl)benzenesulfonamide: 10%
attapulgite: 10%
Pyrophyllite: 80%

The active ingredient is blended with attapulgite and then passed through a hammer-mill to produce particles substantially all below 200 microns. The ground concentrate is then blended with powdered pyrophyllite until homogeneous.

UTILITY

The compounds of the present invention are active herbicides. They have utility for broad-spectrum pre- and/or post-emergence weed control in areas where complete control of all vegetation is desired, such as around fuel storage tanks, ammunition depots, industrial storage areas, oil-well sites, drive-in theaters, around billboards, highway and railroad structures. By properly selecting rate, time and method of application, some of the compounds of this invention may be used to modify plant growth beneficially, and also to selectively control weeds in crops such as wheat and barley, alfalfa, sugarbeets and beans. Postemergence treatments to control weeds in dry beans and sugarbeets have been quite successful with some of the compounds.

The precise amount of the compounds of Formula I to be used in any given situation will vary according to the particular end result desired, the amount of foliage present, the weeds to be controlled, the crop species involved, the soil type, the formulation and mode of application, weather conditions, etc. Since so many variables play a role, it is not possible to state a rate of application suitable for all situations. Broadly speaking, the compounds of this invention are used at levels of about 0.01 to 20 kg/ha with a preferred range of 0.05 to 10 kg/ha. In general, the higher rates of application from within this range will be selected for adverse conditions or where extended persistence in soil is desired.

The compounds of Formula I may be combined with other herbicides and are particularly useful in combination with the ureas: such as 3-(3,4-dichlorophenyl)-1,1-dimethylurea (diuron); the triazines: such as 2-chloro-4-(ethylamino)-6-(isopropylamino)-s-triazine (atrazine); the uracils: such as 5-bromo-3-sec-butyl-6-methyluracil (bromacil); N-(phosponomethyl)glycine (glyphosate); 3-cyclohexyl-1-methyl-6-dimethylamino-s-triazine-2,4(1H,3H)-dione (hexazinone); N,N-dimethyl-2,2-diphenylacetamide (diphenamid); 2,4-dichlorophenoxyacetic acid (2,4-D) (and closely related compounds); 4-chloro-2-butynyl-3-chlorophenylcarbamate (barban); S-(2,3-dichloroallyl)-diisopropylthiocarbamate (diallate); S-(2,3,3-trichloroallyl-diisopropylthiocarbamate (triallate); 1,2-dimethyl-3,5-diphenyl-1H-pyrazolium methyl sulfate (difenzoquat methyl sulfate); methyl 2-[4-(2,4-dichlorophenoxy)phenoxy]propanoate (diclofop methyl); 4-amino-6-tert-butyl-3-(methylthio)-1,2,4-triazin-5(4H)-one (metribuzin); 3-(3,4-dichlorophenyl)-1-methoxy-1-methylurea (linuron); 3-isopropyl-1H-2,1,3-benzothiodiazin-4(3H)-one-2,2-dioxide (bentazon); α,α,α-trifluoro-2,6-dinitro-N,N-dipropyl-p-toluidine (trifluralin); 1,1'-dimethyl-4,4'-bipyridinium ion (paraquat); monosodium methanearsonate (MSMA); 2-chloro-2',6'-diethyl(methoxymethyl)acetanilide (alachlor); 1,1-dimethyl-3-(α,α,α-trifluoro-m-tolyl)-urea (fluometuron); and 5-[2-chloro-4-(trifluoromethyl)phenoxy]-2-nitrobenzoic acid, methyl ester (acifluorfen-methyl).

TEST A

Seeds of crabgrass (Digitaria spp.), barnyardgrass (*Echinochloa crusgalli*), wild oats (*Avena fatua*), cassia (*Cassia tora*), morningglory (Ipomoea sp.), cocklebur (Xanthium spp.), sorghum, corn, soybean, rice, wheat and nutsedge tubers (*Cyperus rotundus*) were planted in a growth medium and treated pre-emergence with the chemicals dissolved in a non-phytotoxic solvent. At the same time, cotton having five leaves (including cotyledonary ones), bush beans with the second trifoliate leaf expanding, crabgrass and barnyardgrass with two leaves, wild oats with one leaf, cassia with three leaves (including cotyledonary ones), morningglory and cocklebur with four leaves (including the cotyledonary ones), sorghum and corn with three leaves, soybean with two cotyledonary leaves, rice with two leaves, wheat with two leaves, and nutsedge with three to five leaves were sprayed. Treated plants and controls were maintained in a greenhouse for sixteen days, then all species were compared to controls and visually rated for response to treatment as recorded in Table A.

The ratings are based on a numerical scale extending from 0=no injury, to 10=complete kill. The accompanying descriptive symbols have the following meanings:
G=growth retardation;
C=chlorosis/necrosis;
E=emergence inhibition;
H=formative effects;
6Y=abscised buds or flowers
U=unusual pigmentation; and
X=axillary stimulation
-=not rated

TABLE A

| Compound | kg/ha | BUSH BEAN | COT-TON | MORNING-GLORY | COCK-LEBUR | CASSIA | NUT-SEDGE | CRAB-GRASS | BARNYARD-GRASS | WILD OATS | WHEAT | CORN | SOY-BEAN | RICE | SORGHUM |
|---|---|---|---|---|---|---|---|---|---|---|---|---|---|---|---|
| | | | | | | POST-EMERGENCE | | | | | | | | | |
| SO₂CH₃ / SO₂NHCN(CH₃)— pyrimidine(OCH₃)₂ | .05 | 5G | 1C,1H | 5C,9G | 5G | 6C,9G | 2C,8G,5X | 2C,9G | 9C | 2C,9G | 2C,8G | 5U,9C | 9C | 5C,9G | 9G |
| SO₂CH₂CH₂CH₃ / SO₂NHCN(CH₃)— pyrimidine(OCH₃)₂ | .05 | 2G | — | 5C,9G | 1C,5G | 3C,5G | 1C,6G | 1C,9G | 9C | 3G | 2G | 1U,6H | 1C,4G | 4C,9G | 3C,9H |
| SO₂CH₂CH₂CH₃ / SO₂NHCN(CH₃)— triazine(OCH₃)(CH₃) | 0.4 | 3C,6Y | 5C,8G | 3C,6G | 5C,8G | 9C | 0 | 1C,5G | 9C | 2C,5G | 0 | | 2C,2H | 8G | 9G |
| SO₂CH₃ / SO₂NHCN(CH₃)— triazine(OCH₃)(CH₃) | 0.4 | 6C,6G, 6Y | 5C,8G | 5C,9G | 6C,9G | 3C,9G | 6G | 9C | 9C | 2C,7G | 2U,8G | 3C,9G | 6C,9G | 5C,9G | 3C,9G |
| SO₂CH₃ / SO₂NHCN(CH₃)— triazine(OCH₃)(CH₃) | 0.4 | 0 | 6B,9G | 5C,9G | 9C | 9C | 3G | 9C | | 2C,7G | 2U,8G | 8U,9C | 6C,9G | 5C,9G | 3C,9G |
| SO₂CH₃ / SO₂NHCN(CH₃)— pyrimidine(OCH₃)₂ | 0.1 | | | | 9C | 9C | | 9C | 10C | 6C,9G | 4C,9G | 9C | 5C,9G | 10C | 9C |

TABLE A-continued

| Structure | kg/ha | MORNING-GLORY | COCKLEBUR | CASSIA | NUTSEDGE | CRABGRASS | BARNYARD-GRASS | WILD OATS | WHEAT | CORN | SOYBEAN | RICE | SORGHUM |
|---|---|---|---|---|---|---|---|---|---|---|---|---|---|
| SO₂CH₂CH₂CH₃ / SO₂NHCN(CH₃)- pyrimidine(OCH₃)₂ | 0.1 | 0 | 4C,9G | 3C,9H | 4C,9G | 0 | 2G | 3H | 0 | 0 | 4C,9H | 2H,8G | 1C,6G | 2C,9G |

PRE-EMERGENCE

| Structure | kg/ha | MORNING-GLORY | COCKLEBUR | CASSIA | NUTSEDGE | CRABGRASS | BARNYARD-GRASS | WILD OATS | WHEAT | CORN | SOYBEAN | RICE | SORGHUM |
|---|---|---|---|---|---|---|---|---|---|---|---|---|---|
| SO₂CH₃ / SO₂NHCN(CH₃)- pyrimidine(OCH₃)₂ | .05 | 0 | 5G | 0 | 0 | 0 | 0 | 0 | 0 | 0 | 0 | 0 | 0 |
| SO₂CH₂CH₂CH₃ / SO₂NHCN(CH₃)- pyrimidine(OCH₃)₂ | .05 | 0 | 0 | 0 | 0 | 0 | 0 | 0 | 0 | 0 | 0 | 0 | 0 |
| SO₂CH₂CH₂CH₃ / SO₂NHCN(CH₃)- pyrimidine(OCH₃)₂ | 0.4 | 2C,6H | — | 1C | 1C | 0 | 3G | 5G | 2G | 2C,9H | 0 | 3C,9H | 3C,9H |
| SO₂CH₃ / SO₂NHCN(CH₃)- pyrimidine(OCH₃)(CH₃) | 0.4 | 1H | 3G | 0 | 0 | 0 | 2C,8H | 1C | 2G | 2C,9G | 2C,4H | 10E | 2C,9G |

TABLE A-continued
| | 0.1 | 9G | 9H | 5C,9G | 0 | 5C,9G | 0 | 0 | 3C,9G | 5H | 10E | 1C,5G |
|---|---|---|---|---|---|---|---|---|---|---|---|---|
| 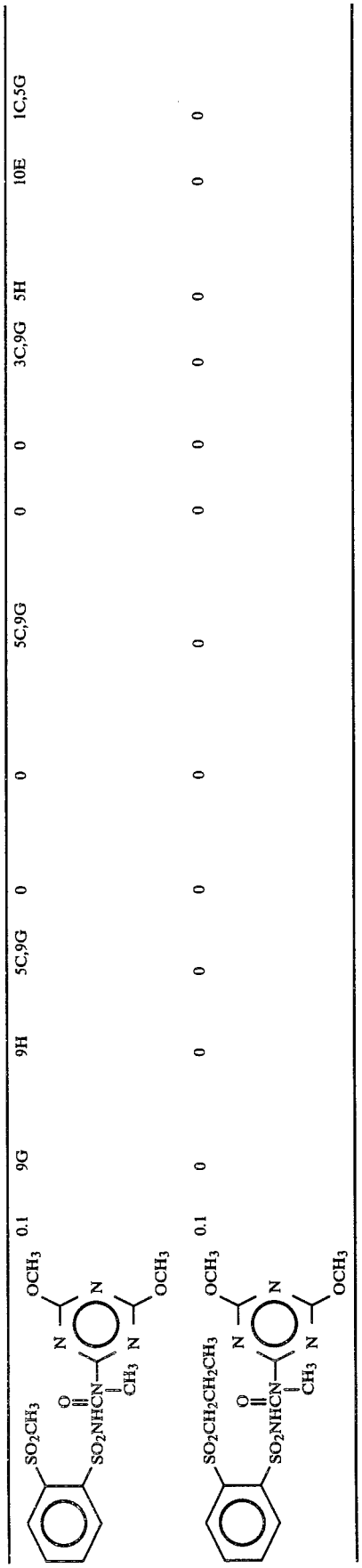 | 0.1 | 0 | 0 | 0 | 0 | 0 | 0 | 0 | 0 | 0 | 0 | 0 |
| | 0.1 | 0 | 0 | 0 | 0 | 0 | 0 | 0 | 0 | 0 | 0 | 0 |

TEST B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B.

TABLE B
PRE-EMERGENCE ON FALLSINGTON SILT LOAM Soil

| Rate kg/ha   | 0.06  | 0.25  | 1     |
|---|---|---|---|
| Crabgrass    | 0     | 0     | 4G    |
| Barnyardgrass| 6G,3H | 9G,9C | 8G,3H |
| Sorghum      | 0     | 4G,3H | 8G,5H |
| Wild Oats    | 0     | 2G    | 3G    |
| Johnsongrass | 0     | 5C    | 3G    |
| Dallisgrass  | 0     | 0     | 0     |
| Giant foxtail| 0     | 0     | 5G,3H |
| Ky. bluegrass| 0     | 0     | 3G,3H |
| Cheatgrass   | 0     | 0     | 0     |
| Sugarbeets   | 0     | 4G    | 10E   |
| Corn         | 3G,2C | 7G,5H | 9G,9C |
| Mustard      | 3G    | 4G    | 8G,7C |
| Cocklebur    | 0     | 0     | 7G,5H |
| Pigweed      | 0     | 4G    | —     |
| Nutsedge     | 0     | 0     | 4G    |
| Cotton       | 3G    | 2G    | 3H    |
| Morningglory | 6G,3H | 6G,3H | 8G    |
| Cassia       | 0     | 0     | 4G,3C |
| Teaweed      | 0     | 0     | 0     |
| Velvetleaf   | 0     | 0     | 8G,3H |
| Jimsonweed   | 0     | 3G    | 7G,5C |
| Soybean      | 0     | 3H    | 7G,5H |
| Rice         | 7G,5C | 4G    | 10E   |
| Wheat        | 0     | 0     | 2G    |

TABLE B-continued
PRE-EMERGENCE ON FALLSINGTON SILT LOAM Soil

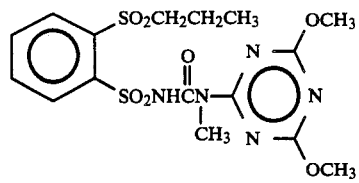

| Rate kg/ha   | 1     |
|---|---|
| Crabgrass    | 3G    |
| Barnyardgrass| 5G    |
| Sorghum      | 6G,3H |
| Wild Oats    | 3G    |
| Johnsongrass | 0     |
| Dallisgrass  | 0     |
| Giant foxtail| 0     |
| Ky. bluegrass| 0     |
| Cheatgrass   | 0     |
| Sugarbeets   | 8G,8C |
| Corn         | 7G,5H |
| Mustard      | 7G,5C |
| Cocklebur    | 5G,2C |
| Pigweed      | —     |
| Nutsedge     | —     |
| Cotton       | 3H    |
| Morningglory | 8G,3C |
| Cassia       | 0     |
| Teaweed      | 0     |
| Velvetleaf   | 5G,5H |
| Jimsonweed   | 0     |
| Soybean      | 2C    |
| Rice         | 5G    |
| Wheat        | 0     |

TEST C

The test chemicals, dissolved in a non-phytotoxic solvent, were applied in an overall spray to the foliage and surrounding soil of selected plant species. One day after treatment, plants were checked for rapid burn injury. Approximately fourteen days after treatment all species were visually compared to untreated controls and rated for response to treatment. The rating system was as described previosly for Test A. The data are presented in Table C.

All plant species were seeded in Woodstown sandy loam soil and grown in a greenhouse. The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), Cassia (*Cassis tora*), monrningglory (*Ipomoea hederacea*), jimsonweed (*Datura stramonium*), cocklebur (*Xanthium pensylvanicum*), crabgrass (Digitaria spp.), nutsedge (*Cyperus rotundus*), barnyardgrass (*Echinochloa crusgalli*), giant foxtail (*Setaria faberii*), and wild oats (*Avena fatua*). The following species were grown in soil in a paper cup (12 cm diameter by 13 cm deep): sunflower, sugarbeets, and mustard. All plants were sprayed approximately 14 days after planting. Additional plant species are sometimes added to this standard test in order to evaluate unusal selectivity.

Several of the compounds tested by this procedure are useful for the postemergence control of weeds in several major crops.

TABLE C

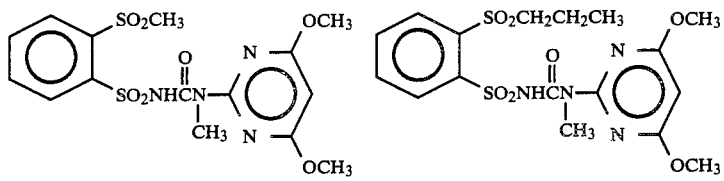

| Rate kg/ha | 0.125 | 0.03 | 0.06 | 0.03 | 0.125 | 0.03 |
|---|---|---|---|---|---|---|
| Soybeans | 10G,9C | 9G,9C | 9G,5C | 5G | 8G,4C | 8G,2C |
| Velvetleaf | 10C | 8G | 7G,2C | 1G | 7G,5C | 7G |
| Sesbania | 10C | 8G,8C | 9G,9C | 7G | 10G,3C | 7G |
| Cassia | 10G,5C | 10G,5C | 3G | 1C | 7G,4C | 5G,4C |
| Cotton | 3G | 4G | 0 | 4G | 8G,2C | 2G |
| Morningglory | 10C | 9G,2C | 8G | 5G | 10G,3C | 10G |
| Alfalfa | 8G | 4G | 5G | 2G | 5G | 5G |
| Jimsonweed | 0 | — | 0 | 0 | 0 | — |
| Cocklebur | 5G | 2G | 4G | 1G | 4G | 3G |
| Corn | 9G,4U | 9G,2I | 8G,7U | 6G,4U | 8G,4H | 5G |
| Crabgrass | 9G | 8G | 7G | 1G | 8G | 1G |
| Rice | 9G,2C | 8G,2C | 7G | 4G | 9G,1C | 9G,3C |
| Nutsedge | 3G | 2G | 0 | 0 | 3G | 4G |
| Barnyardgrass | 9G,4C | 9G,3C | 8G,4C | 8G,3C | 9G,5C | 8G,1C |
| Wheat | 7G,2C | 7G,2C | 5G,2C | 3G | 1C | 0 |
| Giant Foxtail | 9G,9C | 8G | 9G,3U | 2G | 8G | 7G |
| Wild Oats | 7G | 7G | 7G | 5G | 0 | 6G |
| Sorghum | 8G,2U | 7G,6C | 6G | 0 | 9G,3H | 8G,1C |
| Mustard | 9G,9C | 1G | 10C | 4G | 4G | 7G |
| Pigweed | — | — | — | — | — | — |
| Johnsongrass | — | — | — | — | — | — |
| Sunflower | 9C,1C | 7G | 6G | 0 | 5G | 2G |
| Sugarbeets | 4G | 0 | 0 | 1G | 3G | 4G |
| Bush Bean | 4G | 1G | — | — | 0 | 1G |

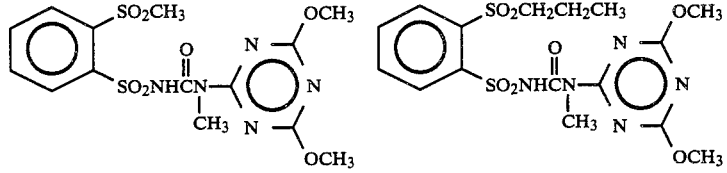

| Rate kg/ha | 0.125 | 0.03 | 0.125 | 0.5 | 0.125 |
|---|---|---|---|---|---|
| Soybeans | 10G,5C | 10G,7C | 10G,5C | 10G,7C | 10G,6C |
| Velvetleaf | 8G,4C | 8G,3C | 8G,5C | 10C | 8G,6C |
| Sesbania | 10G,7C | 9G,2C | 10C | 10C | 9G,5C |
| Cassia | 10G,7C | 9G,1C | 10G,5C | 10G,5C | 9G,5C |
| Cotton | 8G,3C | 8G,3C | 8G,5C | 9G,6C | 9G,6C |
| Morningglory | 9G,2C | 8G,3C | 9G,8C | 10C | 9G,5C |
| Alfalfa | 5G | 0 | 5G | 7G | 7G |
| Jimsonweed | — | — | 1G | — | 0 |
| Cocklebur | 10G,7C | 9G,3C | 10G,9C | 10G,9C | 9G,7C |
| Corn | 9G,7C | 9G,7C | 10C | 9G,1U | 9G,1U |
| Crabgrass | 9G,3C | 5G | 8G,5C | 1G | 0 |
| Rice | 9G,7C | 8G,4C | 9G,8C | 9G,7C | 6G |
| Nutsedge | 0 | 0 | 0 | 4G | 4G |
| Barnyardgrass | 10C | 9C | 9G,4C | 8G,2C | 7G,2C |
| Wheat | 0 | 0 | 5G | 1G | 1G |
| Giant Foxtail | — | — | 2G | 3G | 0 |
| Wild Oats | 0 | 0 | 4G | 4G | 4G |
| Sorghum | 9G | 9G | 7G,1U | 8G,1U | 8G,1U |
| Mustard | — | — | 10C | 10C | 10C |
| Pigweed | — | — | — | — | — |
| Johnsongrass | — | — | — | — | — |
| Sunflower | — | — | 10G,9C | 10C | 10C |
| Sugarbeets | — | — | 9G | 7G | 6G |
| Bush Bean | 2C | 2G | — | — | — |

What is claimed is:

1. A compound of the formula:

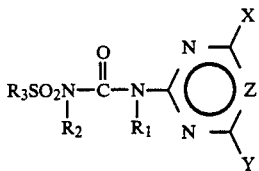 (I)

wherein $R_1$ is H, alkyl of one to three carbon atoms or —OCH$_3$;

$R_2$ is H or alkyl of one to three carbon atoms;

$R_3$ is

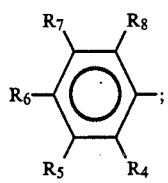

$R_7$ is hydrogen, fluorine, chlorine, bromine, alkyl of 1–4 carbon atoms, alkoxy of 1–4 carbon atoms, nitro, CF$_3$, CH$_3$S or CH$_3$CH$_2$S;

$R_4$ is $R_9$S(O)$_n$;

$R_5$, $R_6$ and $R_8$ are independently hyrogen, fluorine, chlorine, bromine, methyl or methoxy;

$R_9$ is C$_1$–C$_4$ alkyl;

X is —CH$_3$, —CH$_2$CH$_3$, alkoxy of one to three carbons, CF$_3$, CH$_3$S—, CH$_3$OCH$_2$— or CH$_3$OCH$_2$CH$_2$O—;

Y is CH$_3$ or OCH$_3$;

Z is CH; and n is 0, 1 or 2;

and their agriculturally suitable salts; provided that:

(a) $R_1$ and $R_2$ may not simultaneously be hydrogen;

(b) when $R_6$ is other than H, then $R_5$, $R_7$ and $R_8$ must be hydrogen;

(c) when n is 1, then $R_7$ is other than CH$_3$S or CH$_3$CH$_2$S, and X is other than CH$_3$S;

(d) when $R_6$ is H and $R_5$, $R_7$ and $R_8$ are other than H, then $R_5$, $R_7$ and $R_8$ must either be Cl or CH$_3$; and (e) when $R_9$ is C$_1$–C$_2$ alkyl, then n is 1 or 2.

2. A compound of claim 1 wherein $R_7$ is H, Cl, F, Br, CH$_3$, OCH$_3$, CF$_3$ or NO$_2$, and $R_1$ is H or CH$_3$.

3. A compound of claim 2 wherein $R_5$, $R_6$ and $R_8$ are H.

4. A compound of claim 3 wherein $R_2$ is H or CH$_3$.

5. A compound of claim 4 wherein X is CH$_3$, OCH$_3$, OC$_2$H$_5$ or CH$_2$OCH$_3$.

6. A compound of claim 5 wherein $R_9$ is C$_1$–C$_4$ alkyl and n is 2.

7. A compound of claim 6 wherein $R_7$ is H.

8. A compound of claim 7 wherein $R_2$ is H and $R_1$ is CH$_3$.

9. A compound of claim 8 wherein $R_9$ is CH$_3$.

10. The compound of claim 1 which is, N-[(4,6-dimethoxypyrimidin-2-yl)(methyl)aminocarbonyl]-2-(methylsulfonyl)benzenesulfonamide.

11. The compound of claim 1 which is, N-[(4,6-dimethylpyrimidin-2-yl)(methyl)aminocarbonyl]-2-(methylsulfonyl)benzenesulfonamide.

12. The compound of claim 1 which is, N-[(4-methyl-6-methoxypyrimidin-2-yl)(methyl)aminocarbonyl]-2-(methylsulfonyl)benzenesulfonamide.

13. The compound of claim 1 which is, N-[(4,6-dimethoxypyrimidin-2-yl)(methyl)aminocarbonyl]-2-(propylsulfonyl)benzenesulfonamide.

14. A composition suitable for controlling the growth of undesired vegetation which comprises an effective amount of a compound of claim 1 and at least one of the following: surfactant, solid or liquid diluent.

15. A composition suitable for controlling the growth of undesired vegetation which comprises an effective amount of a compound of claim 2 and at least one of the following: surfactant, solid or liquid diluent.

16. A composition suitable for controlling the growth of undesired vegetation which comprises an effective amount of a compound of claim 3 and at least one of the following: surfactant, solid or liquid diluent.

17. A composition suitable for controlling the growth of undesired vegetation which comprises an effective amount of a compound of claim 4 and at least one of the following: surfactant, solid or liquid diluent.

18. A composition suitable for controlling the growth of undesired vegetation which comprises an effective amount of a compound of claim 5 and at least one of the following: surfactant, solid or liquid diluent.

19. A composition suitable for controlling the growth of undesired vegetation which comprises an effective amount of a compound of claim 6 and at least one of the following: surfactant, solid or liquid diluent.

20. A composition suitable for controlling the growth of undesired vegetation which comprises an effective amount of a compound of claim 7 and at least one of the following: surfactant, solid or liquid diluent.

21. A composition suitable for controlling the growth of undesired vegetation which comprises an effective amount of the compound of claim 8 and at least one of the following: surfactant, solid or liquid diluent.

22. A method for controlling the growth of undesired vegetation which comprises applying to the locus to be protected an effective amount of a compound of claim 1.

23. A method for controlling the growth of undesired vegetation which comprises applying to the locus to be protected an effective amount of a compound of claim 2.

24. A method for controlling the growth of undesired vegetation which comprises applying to the locus to be protected an effective amount of a compound of claim 3.

25. A method for controlling the growth of undesired vegetation which comprises applying to the locus to be protected an effective amount of a compound of claim 4.

26. A method for controlling the growth of undesired vegetation which comprises applying to the locus to be protected an effective amount of a compound of claim 5.

27. A method for controlling the growth of undesired vegetation which comprises applying to the locus to be protected an effective amount of a compound of claim 6.

28. A method for controlling the growth of undesired vegetation which comprises applying to the locus to be protected an effective amount of a compound of claim 7.

29. A method for controlling the growth of undesired vegetation which comprises applying to the locus to be protected an effective amount of the compound of claim 8.

* * * * *